(12) United States Patent
Beers et al.

(10) Patent No.: US 9,540,329 B2
(45) Date of Patent: Jan. 10, 2017

(54) ORGANIC ELECTROLUMINESCENT MATERIALS AND DEVICES

(75) Inventors: Scott Beers, Flemington, NJ (US); Chuanjun Xia, Lawrenceville, NJ (US); Suman Layek, Lawrenceville, NJ (US); Harvey Wendt, Medford Lakes, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 923 days.

(21) Appl. No.: 13/553,495

(22) Filed: Jul. 19, 2012

(65) Prior Publication Data

US 2014/0021447 A1 Jan. 23, 2014

(51) Int. Cl.
*H01L 51/50* (2006.01)
*C07D 213/74* (2006.01)
(Continued)

(52) U.S. Cl.
CPC ........... *C07D 213/74* (2013.01); *C07D 401/04* (2013.01); *C07F 15/0033* (2013.01); *C09K 11/06* (2013.01);
(Continued)

(58) Field of Classification Search
CPC .. H01L 51/50; H01L 51/5016; H01L 51/0085; C07F 15/0033; C09K 11/06; C09K 2211/1007; C09K 2211/1011; C09K 2211/1014; C09K 2211/1029; C09K 2211/1044; C09K 2211/185
(Continued)

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

EP 0650955 5/1995
EP 1725079 11/2006
(Continued)

OTHER PUBLICATIONS

Gao et al., High efficiency polymer electrophosphorescent light-emitting diodes, Jun. 27, 2005, Semiconductor Science and Technology, vol. 20, pp. 805-808.*
(Continued)

*Primary Examiner* — Jennifer Chriss
*Assistant Examiner* — Dylan Kershner
(74) *Attorney, Agent, or Firm* — Duane Morris LLP

(57) ABSTRACT

Heteroleptic complexes having at least one diarylamino or carbazole group, as shown in Formula (I), are provided:

(Continued)

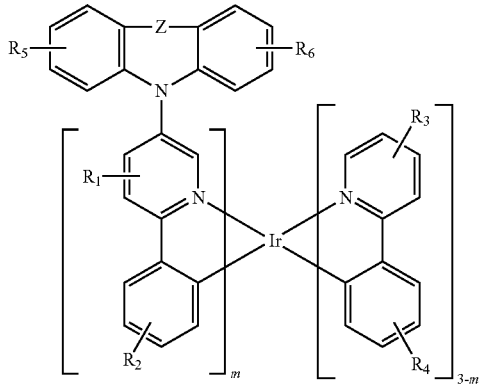

(I)

wherein $R_1$, $R_2$, $R_3$, $R_4$, $R_5$, and $R_6$ each represent mono, di, tri, tetra, or penta substitutions or no substitution; wherein Z is a single bond connecting the two phenyl rings, or is absent, wherein when Z is absent, the positions on the phenyl rings may be substituted by $R_5$ or $R_6$; wherein any two adjacent substituents are optionally joined together to form a ring, which may be further substituted; wherein each of $R_1$, $R_2$, $R_3$, $R_4$, $R_5$, and $R_6$ is independently selected from various substituents; and wherein m is 1 or 2. Devices, such as organic light emitting devices (OLEDs) that comprise phosphorescent light emitting materials are also provided.

18 Claims, 3 Drawing Sheets

(51) Int. Cl.
    *C09K 11/06* (2006.01)
    *C07D 401/04* (2006.01)
    *C07F 15/00* (2006.01)
    *H05B 33/10* (2006.01)
    *H01L 51/00* (2006.01)

(52) U.S. Cl.
    CPC ....... *H05B 33/10* (2013.01); *C09K 2211/1007* (2013.01); *C09K 2211/1011* (2013.01); *C09K 2211/1014* (2013.01); *C09K 2211/185* (2013.01); *H01L 51/0085* (2013.01); *H01L 51/5016* (2013.01)

(58) Field of Classification Search
    USPC .... 428/690, 917; 257/40, E51.041, E51.044, 257/E51.043; 313/504, 505, 506; 546/4, 546/10; 548/103, 108
    See application file for complete search history.

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Hueschen |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0013905 A1* | 1/2004 | Tsuboyama et al. ......... 428/690 |
| 2004/0036077 A1 | 2/2004 | Ise |
| 2004/0137267 A1* | 7/2004 | Igarashi et al. ............... 428/690 |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0247061 A1* | 10/2007 | Adamovich et al. ......... 313/504 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1* | 4/2009 | Kwong ............... H01L 51/0085 313/504 |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0270540 A1* | 10/2010 | Chung et al. ................... 257/40 |
| 2011/0049497 A1* | 3/2011 | Ise ................. 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |

(56) References Cited

FOREIGN PATENT DOCUMENTS

| WO | 0215645 | 2/2002 |
|---|---|---|
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | WO 2009021126 A2 * | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Mak et al., "Blue-to-green electrophosphorescence of iridium-based cyclometallated materials", Aug. 25, 2005, Chemical Communications, pp. 4708-4710.*
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).
Gao, Zhiqiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 115-20 (2000).
Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi and Tokito, Shizuo, "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Indium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).

(56) References Cited

OTHER PUBLICATIONS

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett, 69(15):2160-2162 (1996).

Wang, Y. et al., "Highly Efficient Electroluminescent Materials Based on Fluorinated Organometallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs). More specifically, the invention relates to phosphorescent light emitting materials that may have improved quantum efficiency and/or increased operational lifetime.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

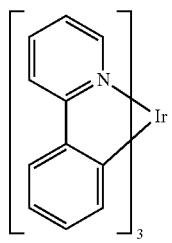

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

A new type of light emitting material is provided, which include heteroleptic complexes having at least one diarylamino or carbazole group, as shown in Formula (I), below:

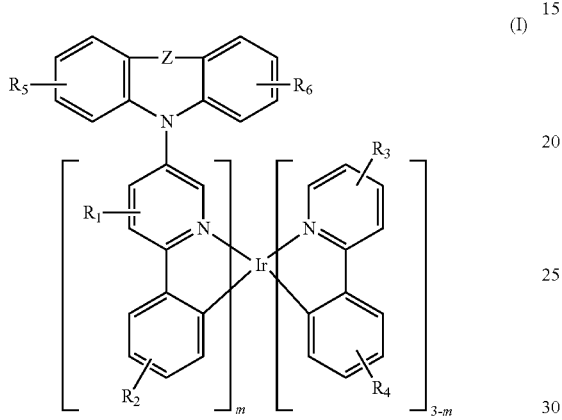

(I)

wherein $R_1$, $R_2$, $R_3$, $R_4$, $R_5$, and $R_6$ each represent mono, di, tri, tetra, or penta substitutions or no substitution; wherein Z is a single bond connecting the two phenyl rings, or is absent, wherein when Z is absent, the positions on the phenyl rings may be substituted by $R_5$ or $R_6$; wherein any two adjacent substituents are optionally joined together to form a ring, which may be further substituted; wherein each of $R_1$, $R_2$, $R_3$, $R_4$, $R_5$, and $R_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein m is 1 or 2.

Heteroleptic complexes of Formula (II) are also provided:

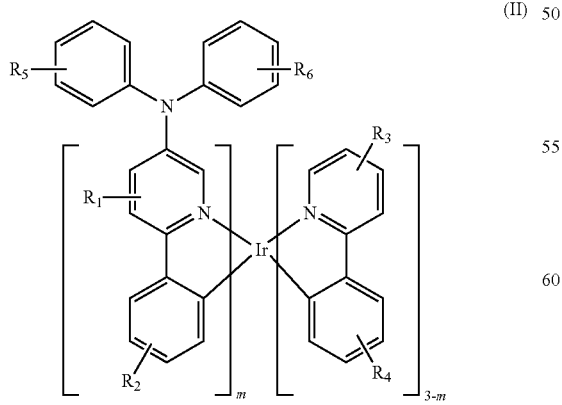

(II)

where the variables have the definitions provided above.

Heterleptic complexes of Formula (III) are also provided:

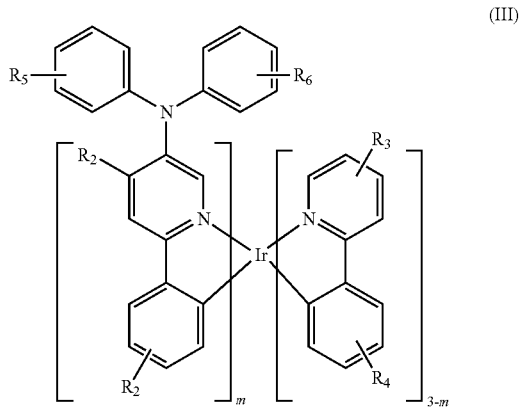

(III)

where the variables have the definitions provided above.

Heteroleptic complexes of Formula (IV) are also provided:

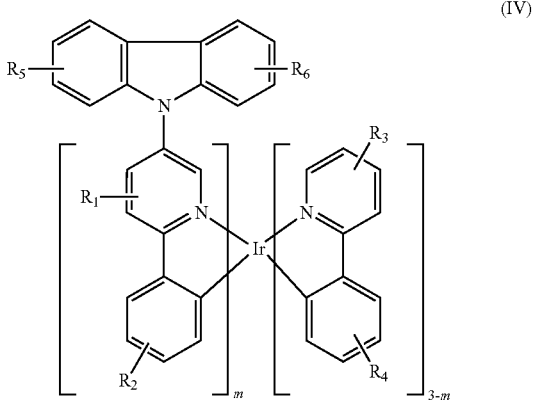

(IV)

where the variables have the definitions provided above.

Heteroleptic complexes of Formula (V) are also provided:

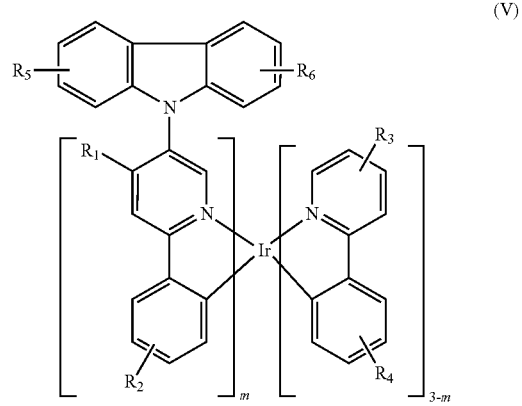

(V)

where the variables have the definitions provided above.

For any of the aforementioned heterleptic complexes, m can have any suitable value. In some embodiments, m is 1. In other embodiments, m is 2.

In some embodiments of the aforementioned heteroleptic complexes, $R_1$, $R_2$, $R_3$, $R_4$, $R_5$, and $R_6$ have the values as provided for the compounds of Formula (I). In some embodiments, however, each of $R_1$, $R_2$, $R_3$, $R_4$, $R_5$, and $R_6$, is selected independently from the group consisting of: hydrogen, deuterium, alkyl, cycloalkyl, aryl, heteroaryl, and combinations thereof. In some other embodiments, each of $R_1$, $R_2$, $R_3$, $R_4$, $R_5$, and $R_6$, is selected independently from the group consisting of: hydrogen, deuterium, alkyl, and combinations thereof. In some further embodiments, each of $R_1$, $R_2$, $R_3$, $R_4$, $R_5$, and $R_6$, is selected independently from the group consisting of: hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof.

Heteroleptic complexes are provided, where the complexes are selected from the group consisting of:

Compound 1

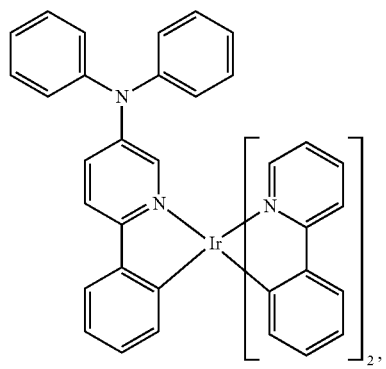

Compound 2

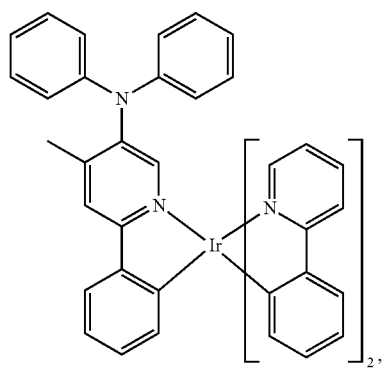

Compound 6

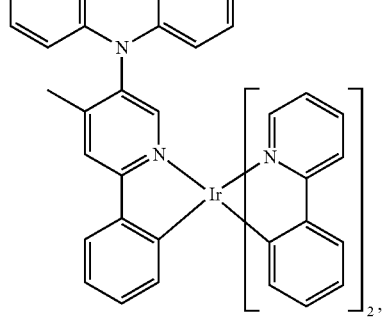

Compound 7

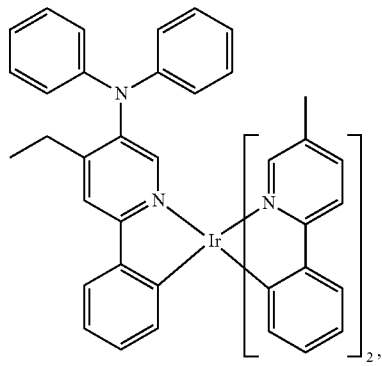

Compound 8

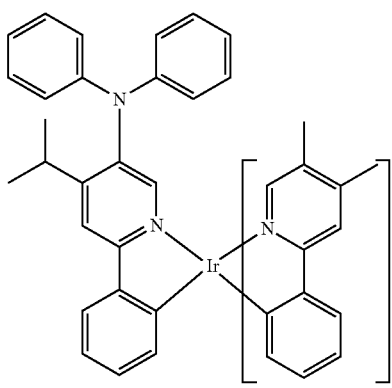

and

Compound 9

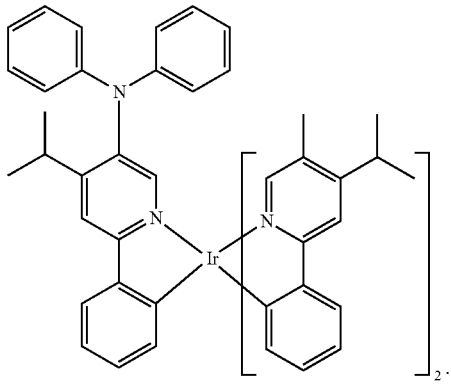

Heteroleptic complexes are provided, where the complexes are selected from the group consisting of:

Compound 27
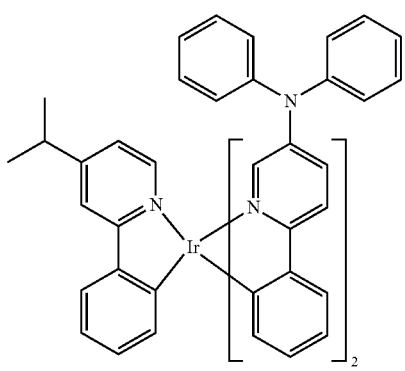
Compound 28
Compound 29
Compound 30
-continued
Compound 31
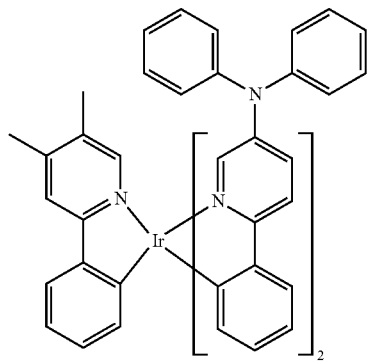
Compound 32
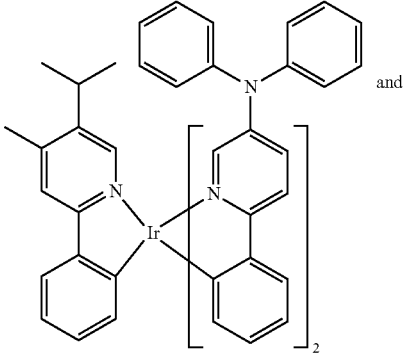
and
Compound 33
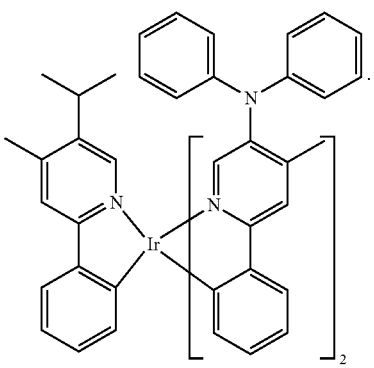
Heteroleptic complexes are provided, where the complexes are selected from the group consisting of:
Compound 4
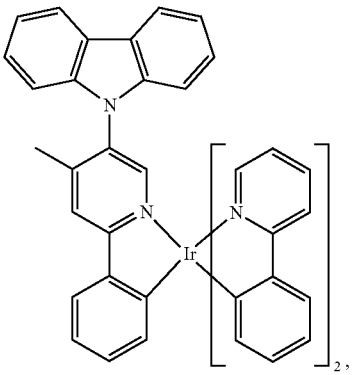

Compound 3
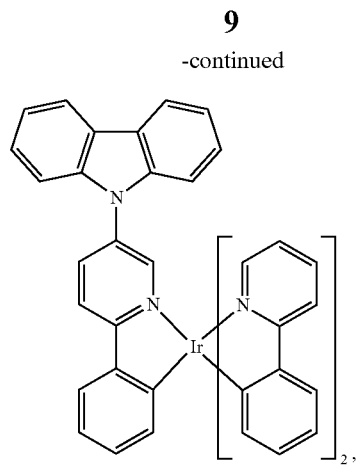
Compound 13
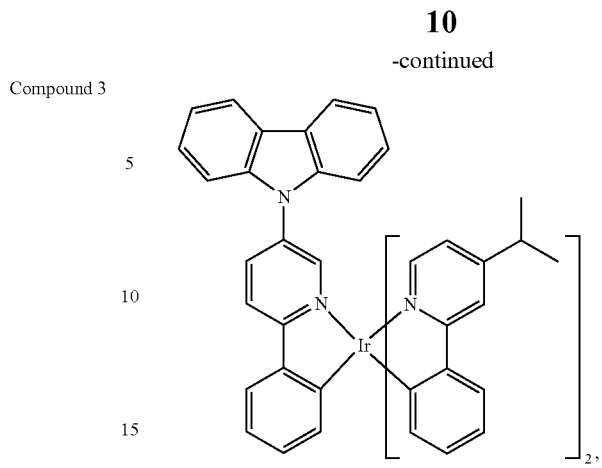
Compound 10
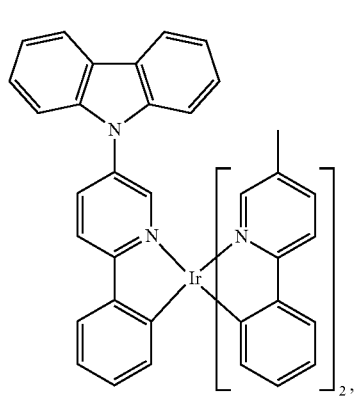
Compound 14
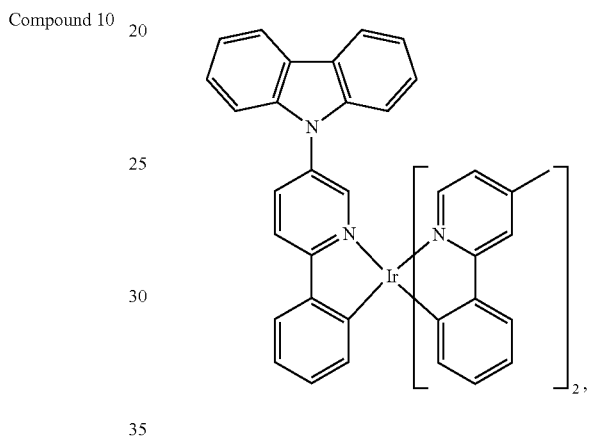
Compound 11
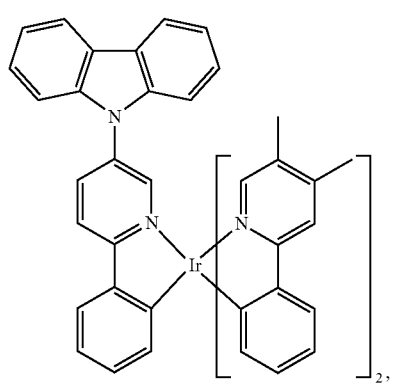
Compound 15
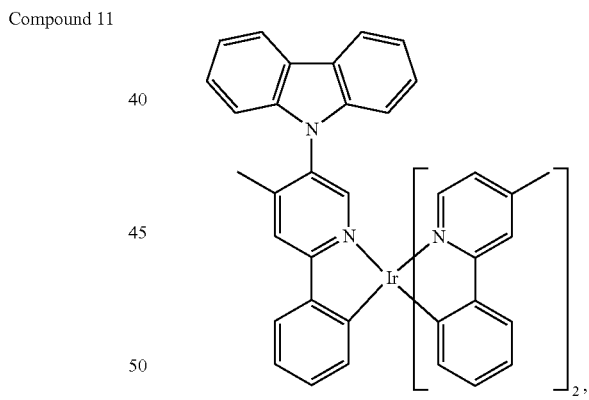
Compound 12
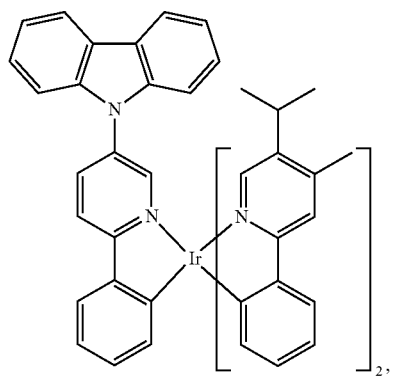
Compound 16
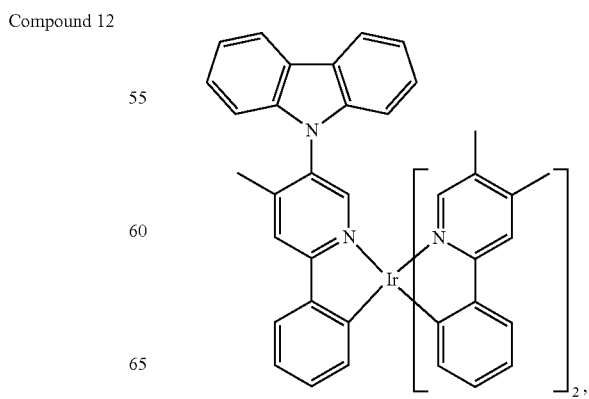

Compound 17
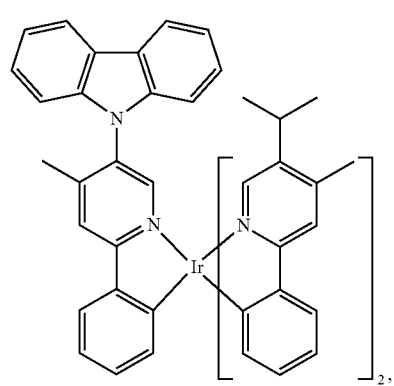
Compound 18
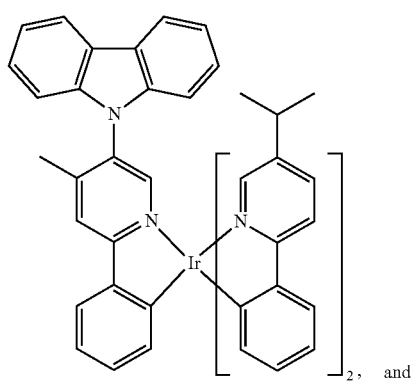
, and
Compound 19
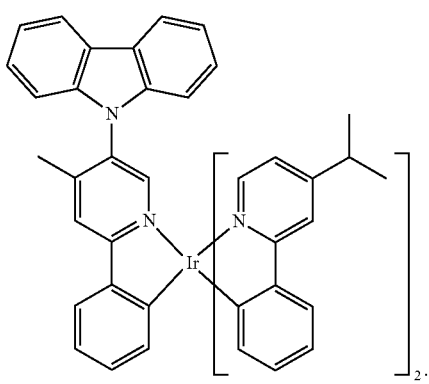
.
Heteroleptic complexes are provided, where the complexes are selected from the group consisting of:
Compound 5
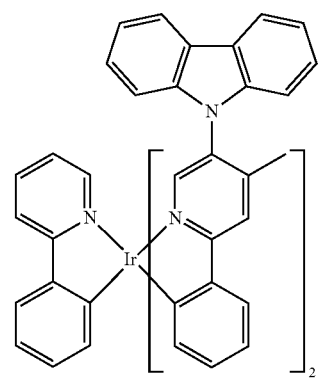
Compound 21
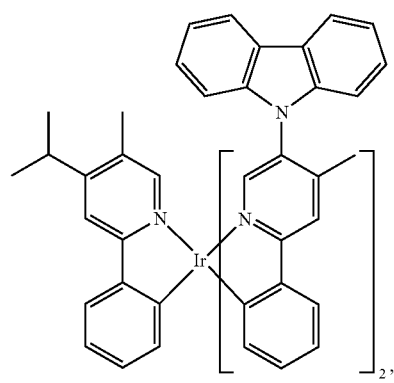
Compound 22
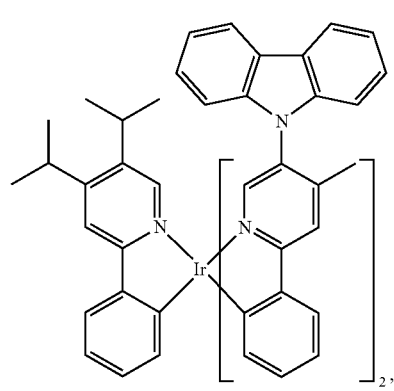
Compound 23
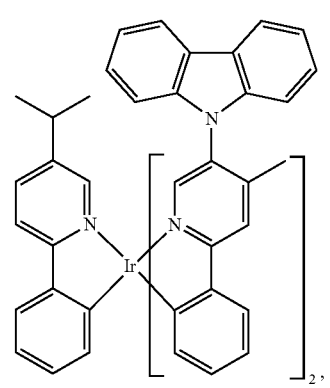
Compound 24
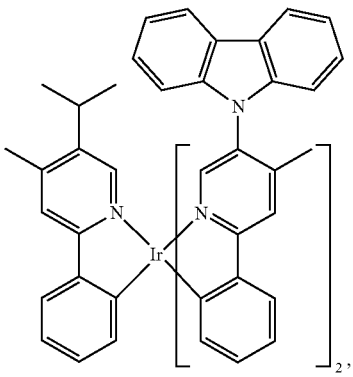

-continued

Compound 25

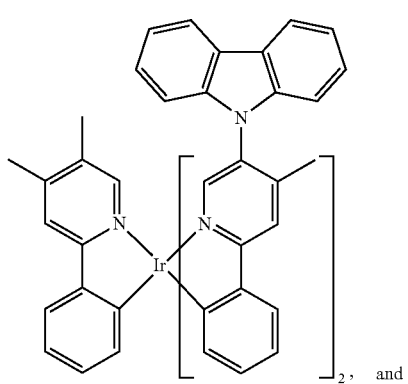

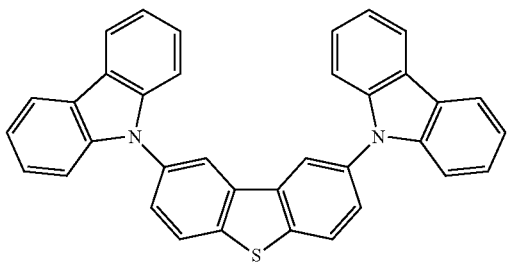

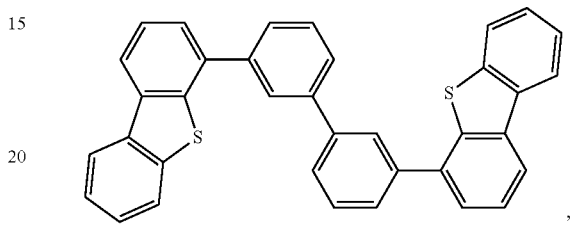

Compound 26

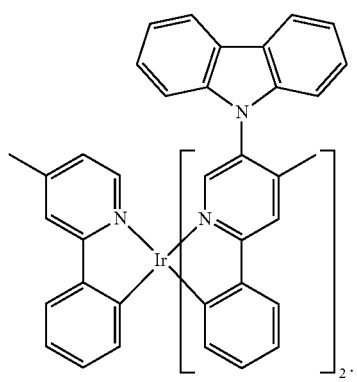

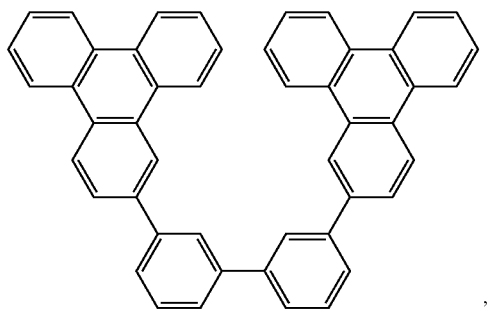

A device is also provided. The device may include an anode, a cathode, and an organic layer disposed between the anode and the cathode, where the organic layer comprises a heteroleptic complex of any of the foregoing embodiments.

The invention is not limited to any particular type of device. In some embodiments, the device is a consumer product. In some embodiments, the device is an organic light emitting device (OLED). In other embodiments, the device comprises a lighting panel.

In some embodiments, the organic layer of the device is an emissive layer. In some such embodiments, the heteroleptic complex is an emissive dopant. In some other embodiments, the heteroleptic complex is a non-emissive dopant.

In some embodiments, the organic layer of the device further comprises a host.

In some such embodiments, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution, wherein n is from 1 to 10, and wherein $Ar_1$ and $Ar_2$ are independently selected from the group consisting of benzene, biphenyl, naphthalene, triphenylene, carbazole, and heteroaromatic analogs thereof. In some such embodiments, the host is a compound selected from the group consisting of:

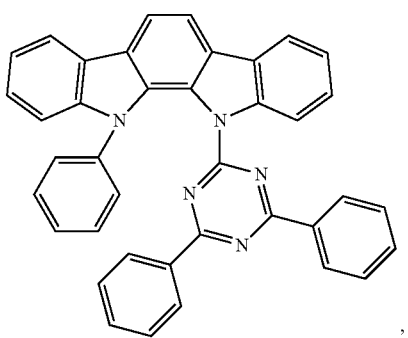

-continued

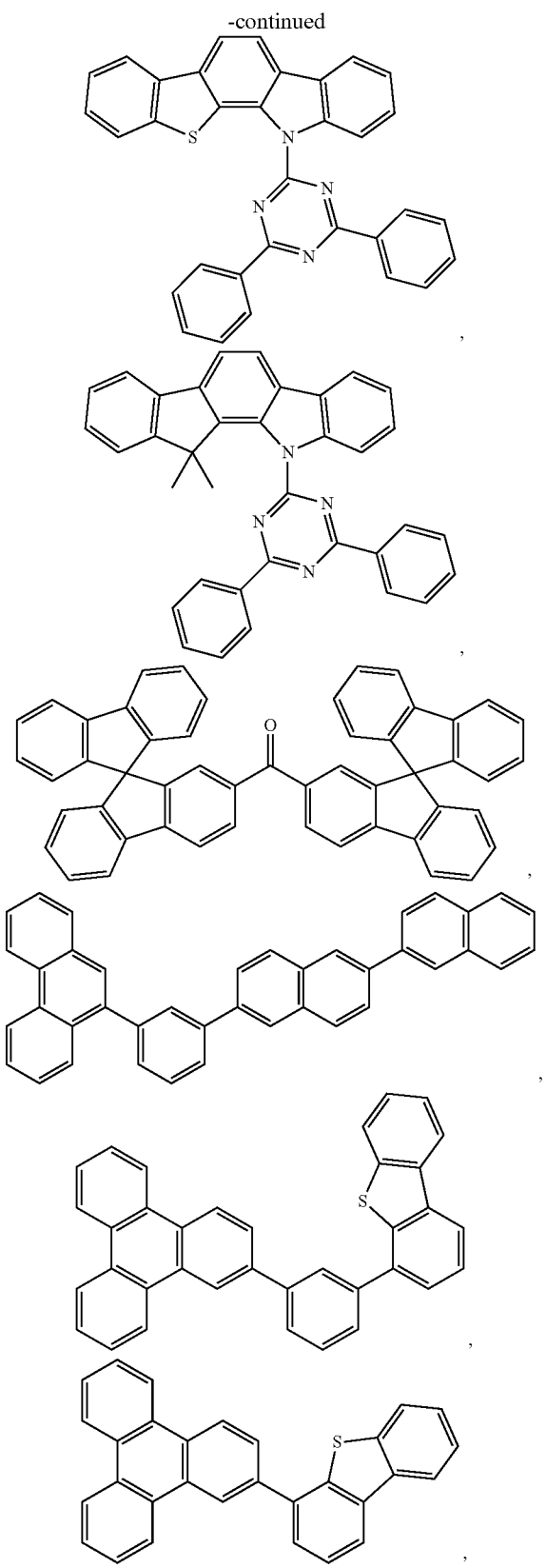

and combinations thereof.

In some other embodiments, the host comprises a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
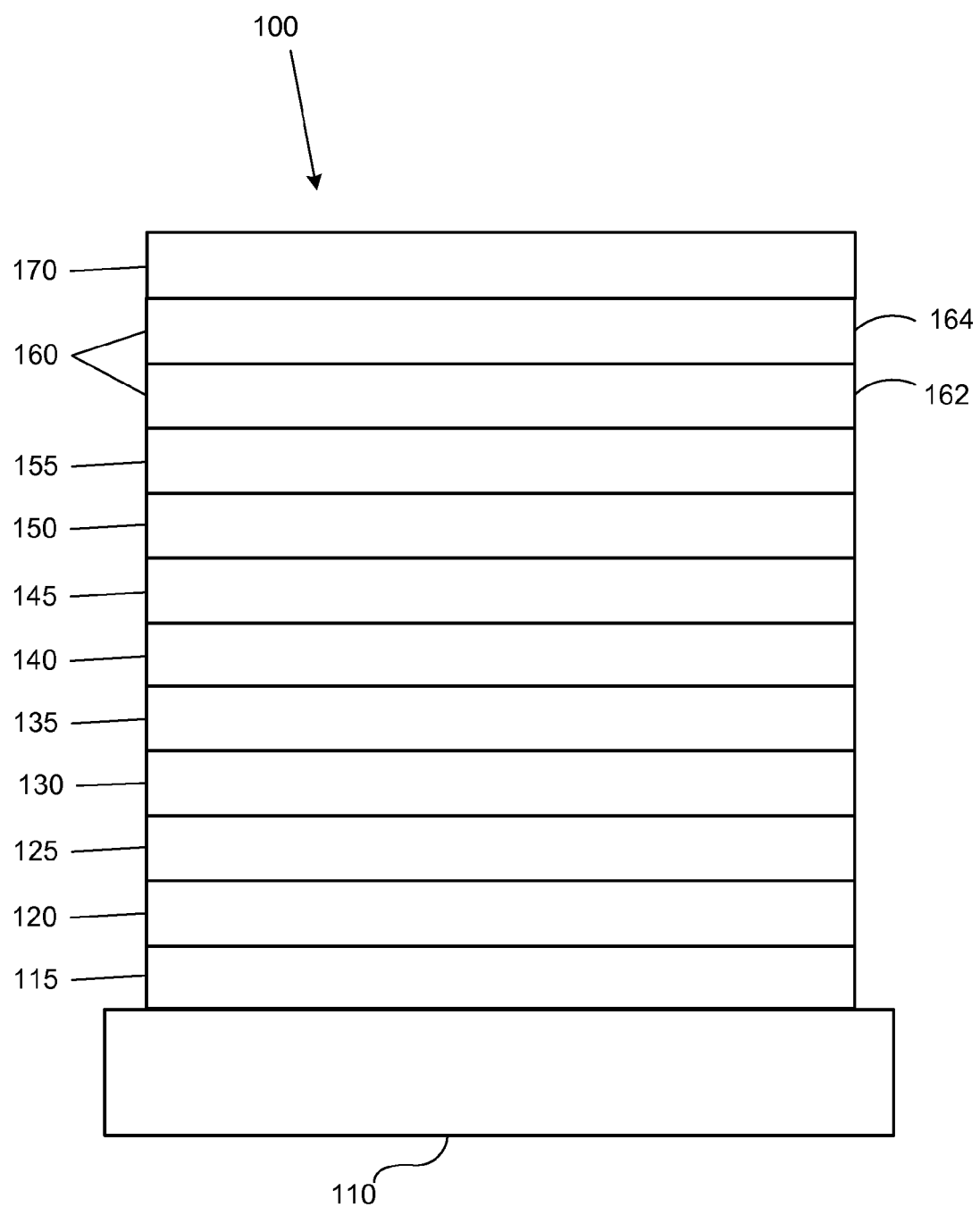
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
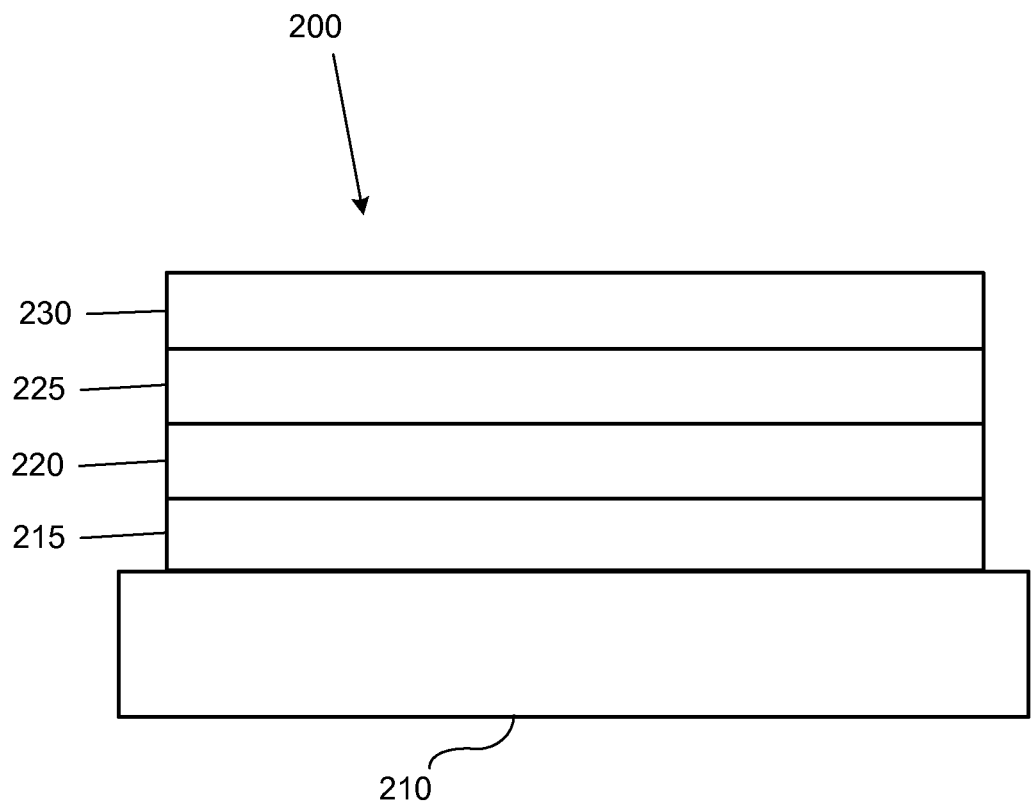
FIG. 2 shows an inverted organic light emitting device that does not have a separate electron transport layer.
Figure 3:
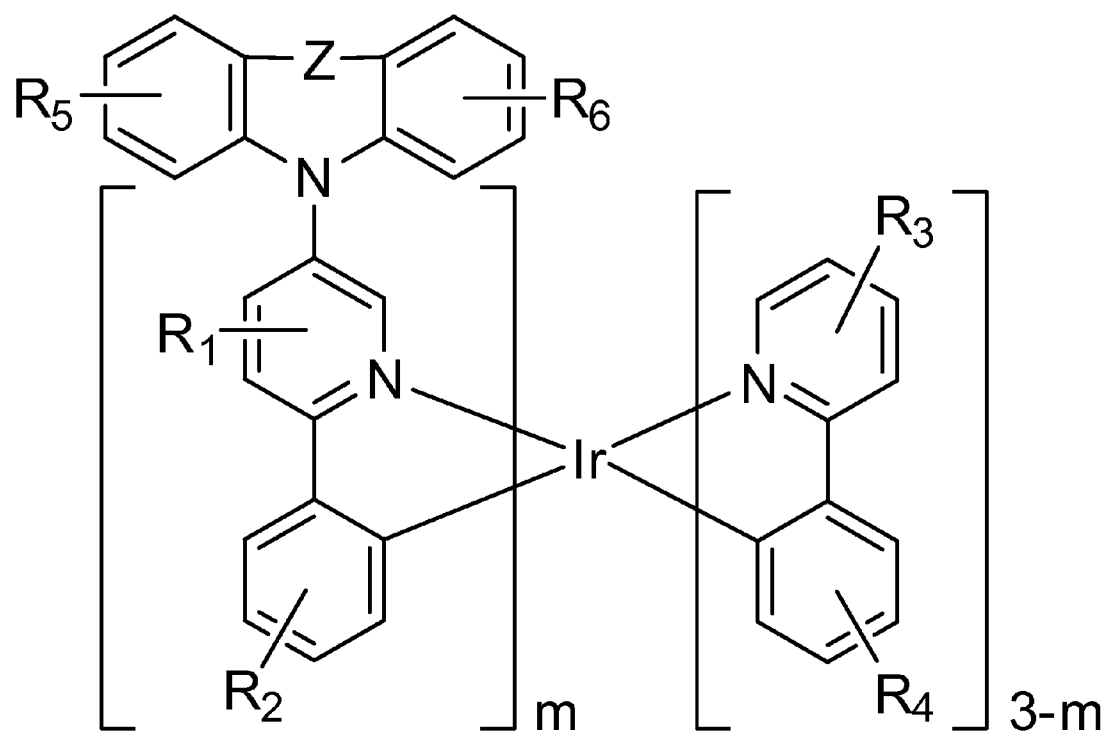
FIG. 3 shows a chemical structure that represents diarylamino- or carbazole-substituted metal complexes, as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Certain 2-phenylpyridine metal complexes yield a green phosphorescent emission. New metal complexes are provided that include a carbazole or diarylamino substituent on the pyridine ring of a 2-phenylpyridine ligand. The diarylamine or carbazole moieties increase conjugation and function as electron donors. Such substitution leads to compounds exhibiting green phosphorescent emission with high quantum efficiency with superior thermal and device stability, which leads to improved operational lifetime.

New heteroleptic metal complexes are provided, where the metal is complexed to at least one 2-phenylpyridine ligand that is further substituted with a carbazole or diarylamino moiety. Such complexes may be advantageously used in OLEDs. Particular such heteroleptic complexes include compounds of Formula (I):

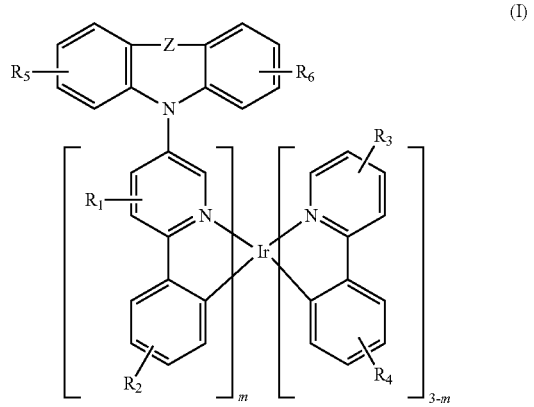

(I)

wherein $R_1$, $R_2$, $R_3$, $R_4$, $R_5$, and $R_6$ each represent mono, di, tri, tetra, or penta substitutions or no substitution; wherein Z is a single bond connecting the two phenyl rings, or is absent, wherein when Z is absent, the positions on the phenyl rings may be substituted by $R_5$ or $R_6$; wherein any two adjacent substituents are optionally joined together to form a ring, which may be further substituted; wherein each of $R_1$, $R_2$, $R_3$, $R_4$, $R_5$, and $R_6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl; aryl, heteroaryl, acyl, carbonyl, carboxylic acids, ester, nitrite, isonitrile, sulfanyl, sulfinyl, sulfonyl, phosphino, and combinations thereof; and wherein m is 1 or 2.

Heteroleptic complexes of Formula (II) are also provided:

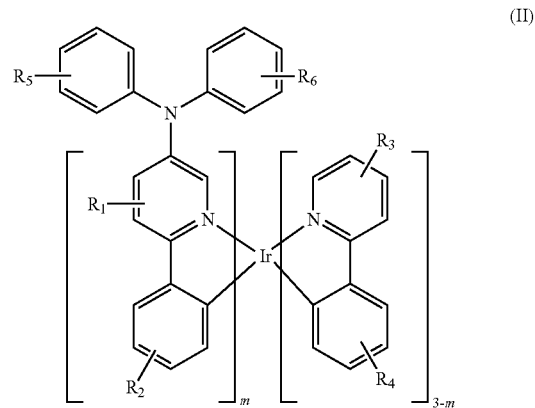

(II)

where the variables have the definitions provided above.

Heterleptic complexes of Formula (III) are also provided:

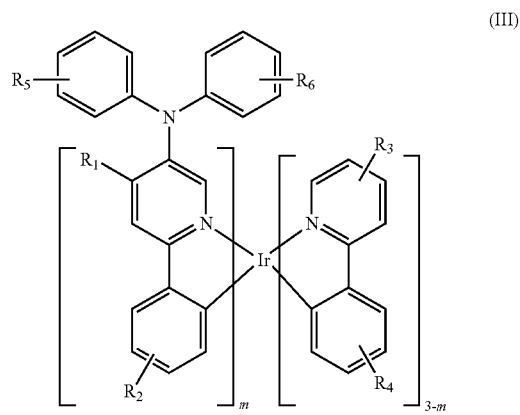

(III)

where the variables have the definitions provided above.

Heteroleptic complexes of Formula (IV) are also provided:

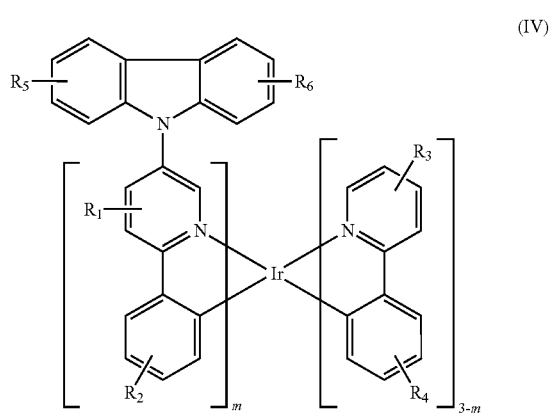

(IV)

where the variables have the definitions provided above.

Heteroleptic complexes of Formula (V) are also provided:

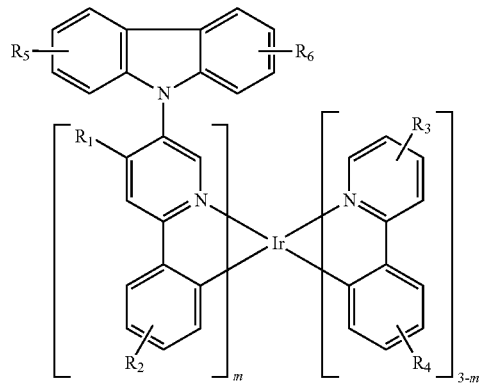

(V)

where the variables have the definitions provided above.

For any of the aforementioned heterleptic complexes, m can have any suitable value. In some embodiments, m is 1. In other embodiments, m is 2.

In some embodiments of the aforementioned heteroleptic complexes, $R_1$, $R_2$, $R_3$, $R_4$, $R_5$, and $R_6$ have the values as provided for the compounds of Formula (I). In some embodiments, however, each of $R_1$, $R_2$, $R_3$, $R_4$, $R_5$, and $R_6$, is selected independently from the group consisting of hydrogen, deuterium, alkyl, cycloalkyl, aryl, heteroaryl, and combinations thereof. In some other embodiments, each of $R_1$, $R_2$, $R_3$, $R_4$, $R_5$, and $R_6$, is selected independently from the group consisting of: hydrogen, deuterium, alkyl, and combinations thereof. In some further embodiments, each of $R_1$, $R_2$, $R_3$, $R_4$, $R_5$, and $R_6$, is selected independently from the group consisting of: hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof.

Heteroleptic complexes are provided, where the complexes are selected from the group consisting of:

Compound 1

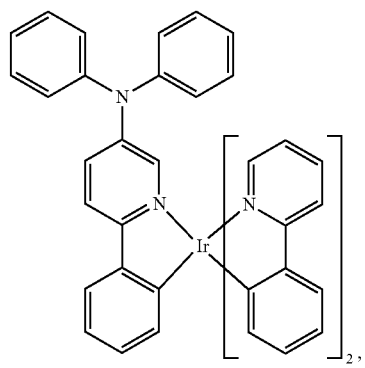

Compound 2

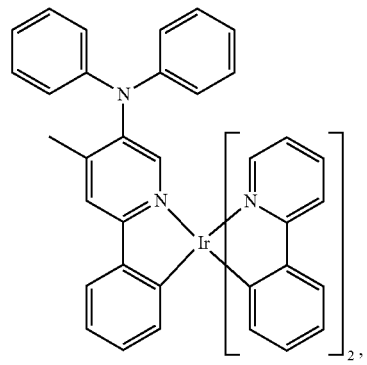

Compound 6

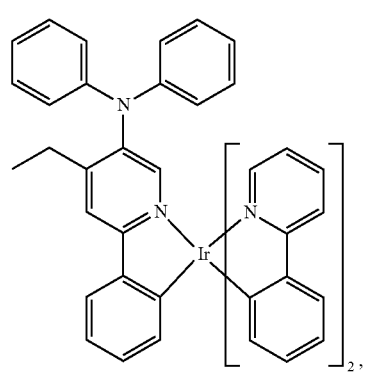

Compound 7

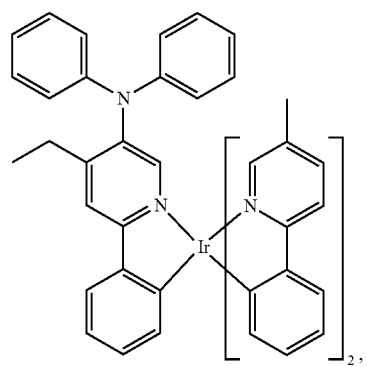

Compound 8

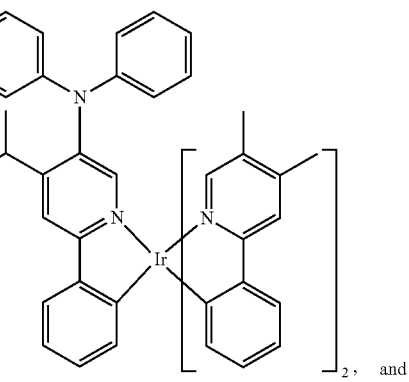

, and

Compound 9
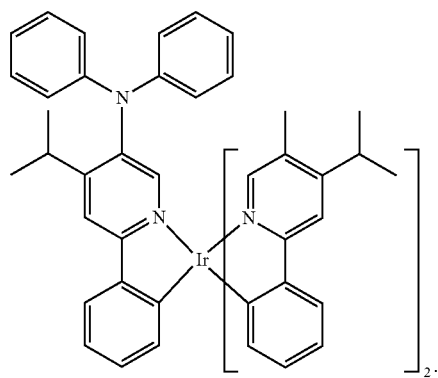
Heteroleptic complexes are provided, where the complexes are selected from the group consisting of:
Compound 27
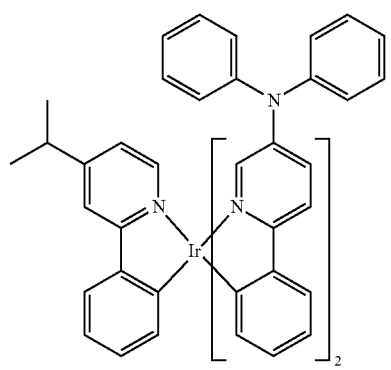
Compound 28
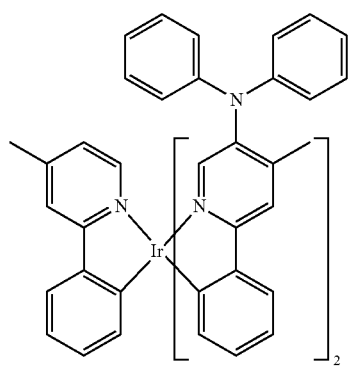
Compound 29
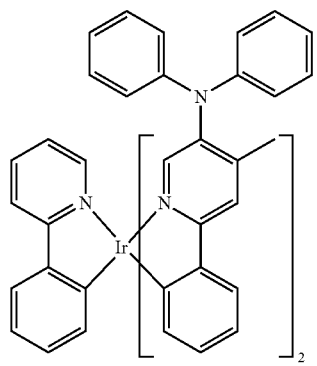
Compound 30
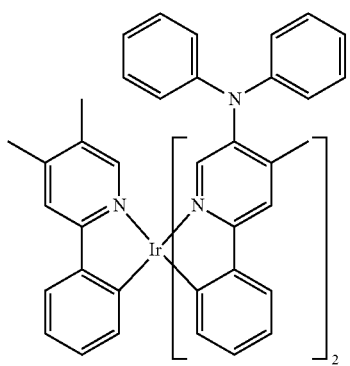
Compound 31
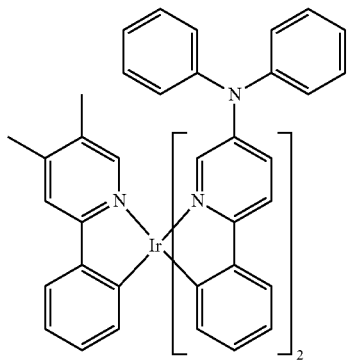
Compound 32
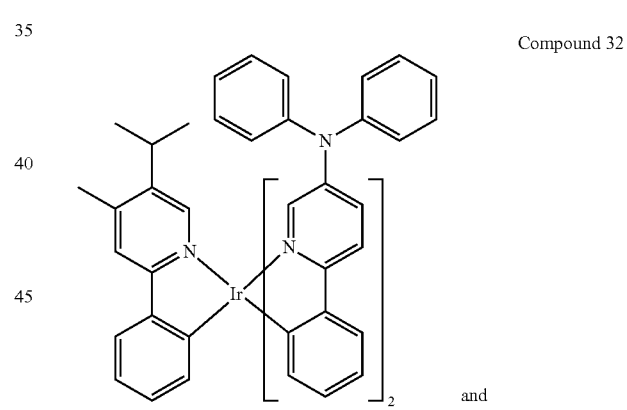
and
Compound 33
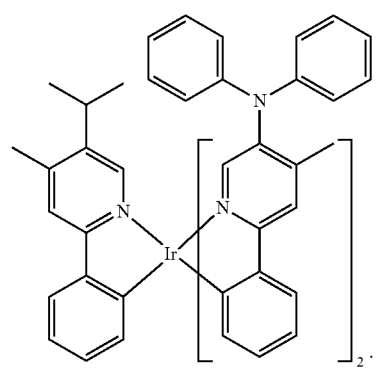
Heteroleptic complexes are provided, where the complexes are selected from the group consisting of:

Compound 4
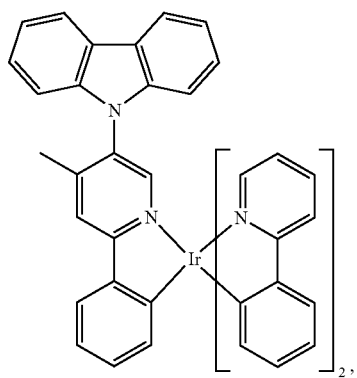
Compound 3
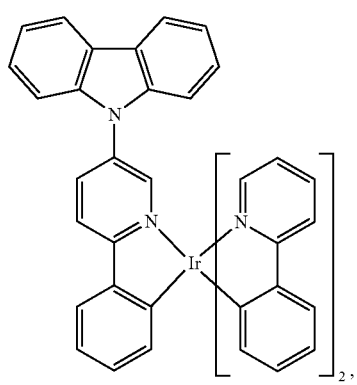
Compound 10
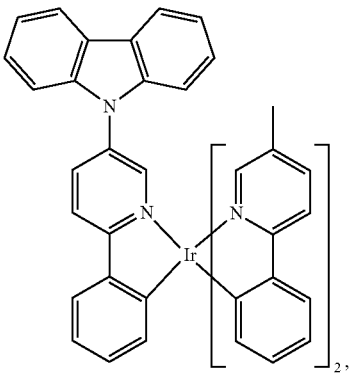
Compound 11
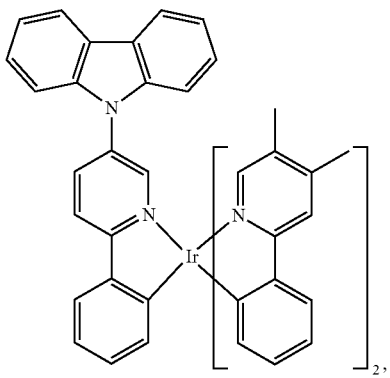
Compound 12
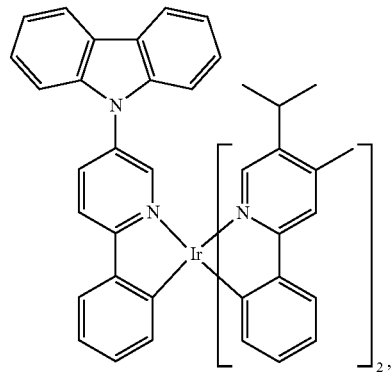
Compound 13
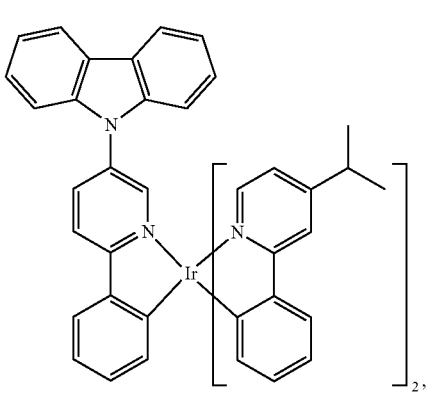
Compound 14
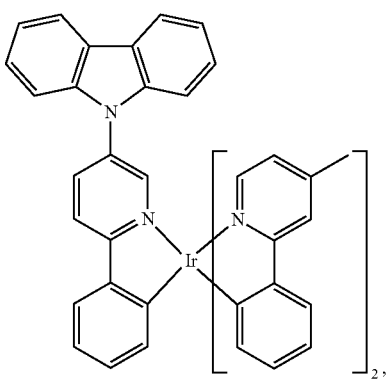
Compound 15
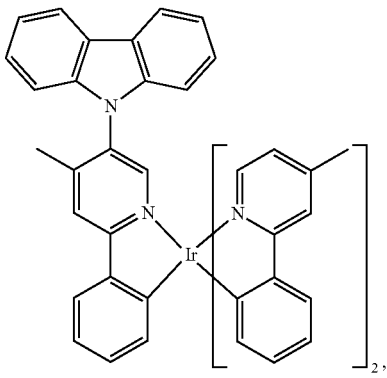

Compound 16
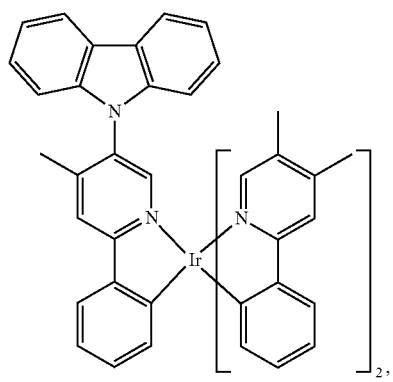
Compound 5
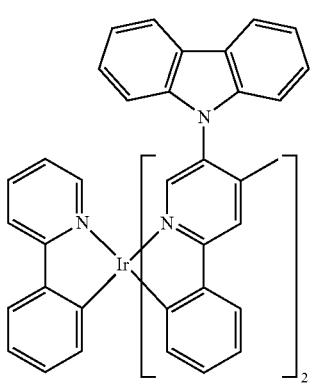
Compound 17
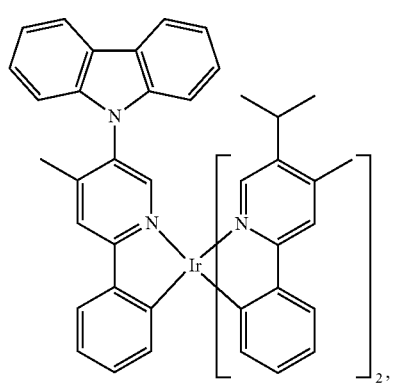
Compound 21
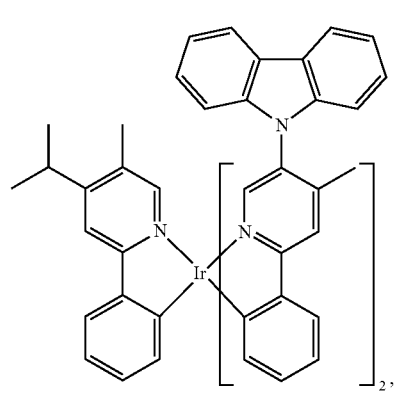
Compound 18
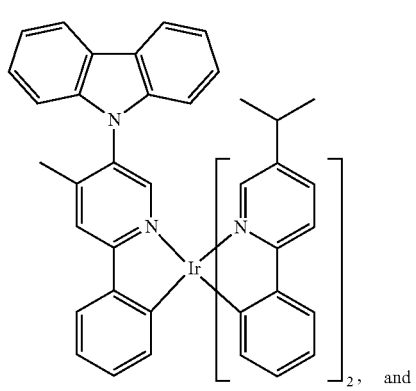
Compound 22
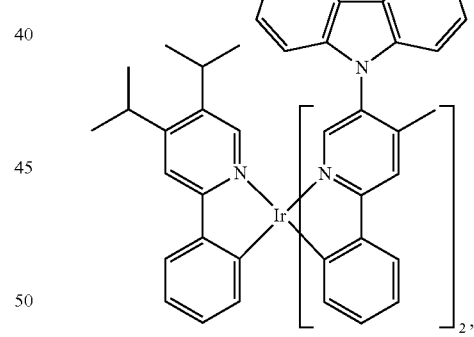
Compound 19
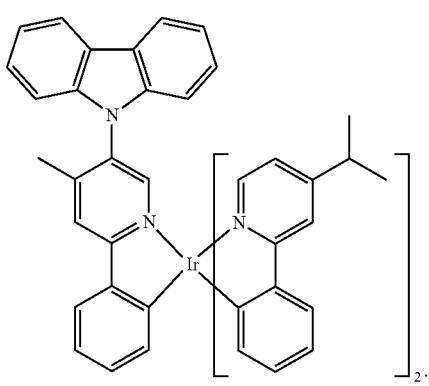
Compound 23
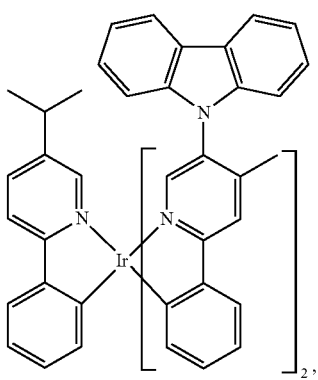
Heteroleptic complexes are provided, where the complexes are selected from the group consisting of:

-continued

Compound 24

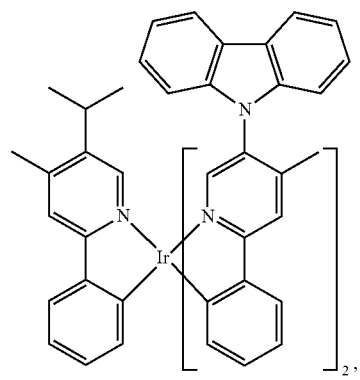

Compound 25

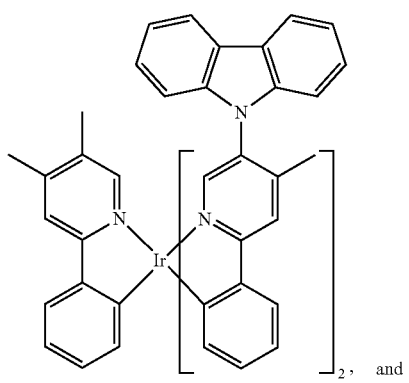, and

Compound 26

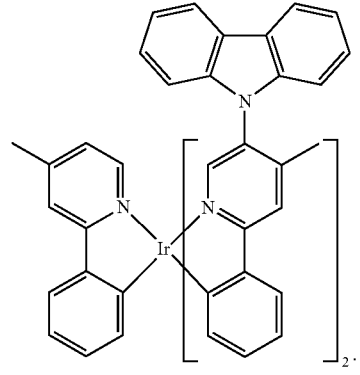.

A device is also provided. The device may include an anode, a cathode, and an organic layer disposed between the anode and the cathode, where the organic layer comprises a heteroleptic complex of any of the foregoing embodiments.

The invention is not limited to any particular type of device. In some embodiments, the device is a consumer product. In some embodiments, the device is an organic light emitting device (OLED). In other embodiments, the device comprises a lighting panel.

In some embodiments, the organic layer of the device is an emissive layer. In some such embodiments, the heteroleptic complex is an emissive dopant. In some other embodiments, the heteroleptic complex is a non-emissive dopant.

In some embodiments, the organic layer of the device further comprises a host.

In some such embodiments, the host comprises a triphenylene containing benzo-fused thiophene or benzo-fused furan, wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution, wherein n is from 1 to 10, and wherein $Ar_1$ and $Ar_2$ are independently selected from the group consisting of benzene, biphenyl, naphthalene, triphenylene, carbazole, and heteroaromatic analogs thereof. In some such embodiments, the host is a compound selected from the group consisting of:

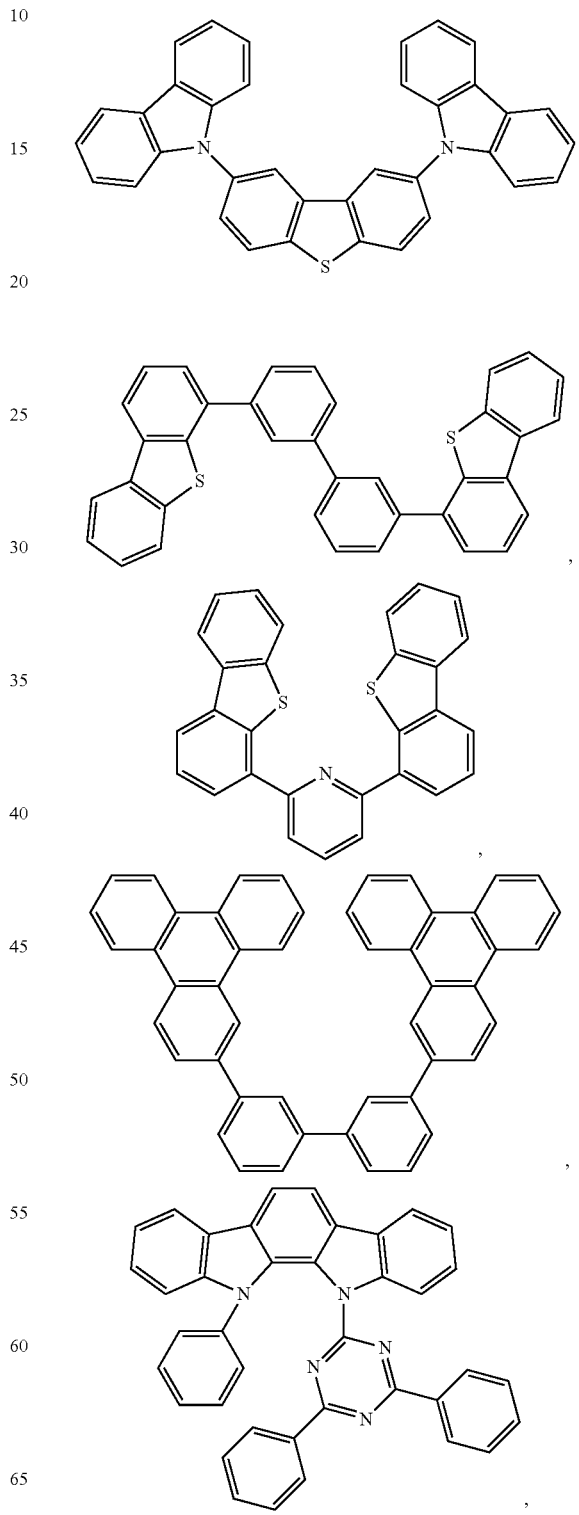

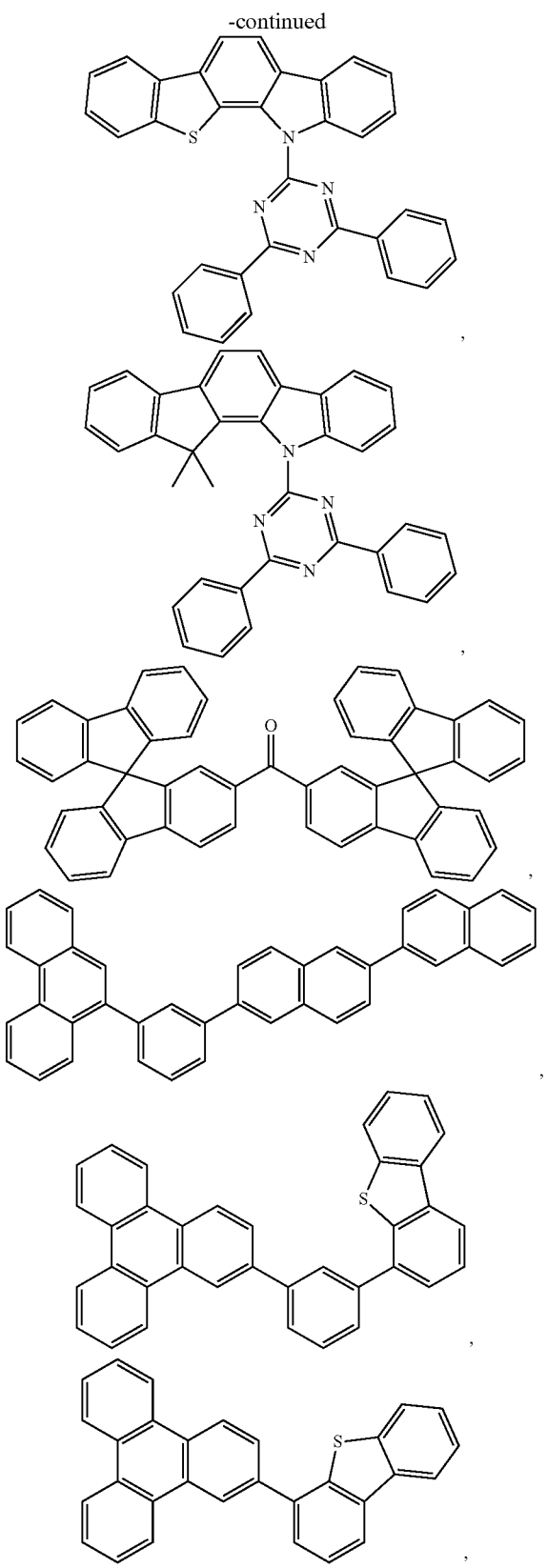

and combinations thereof.

In some other embodiments, the host comprises a metal complex.

Combination with Other Materials

The materials described herein as useful for a particular layer in an organic light emitting device may be used in combination with a wide variety of other materials present in the device. For example, compounds disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

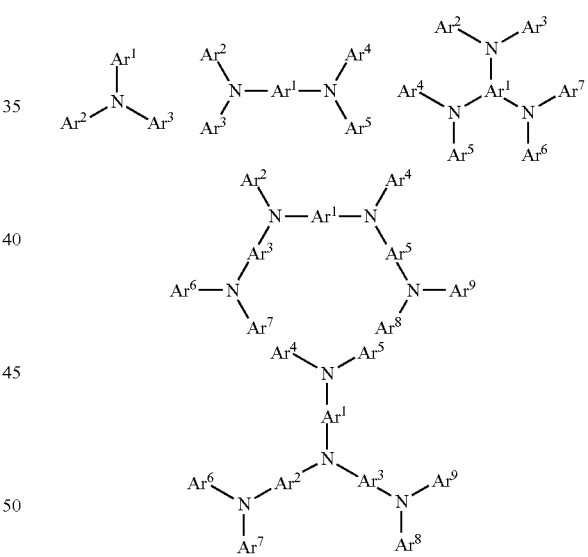

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

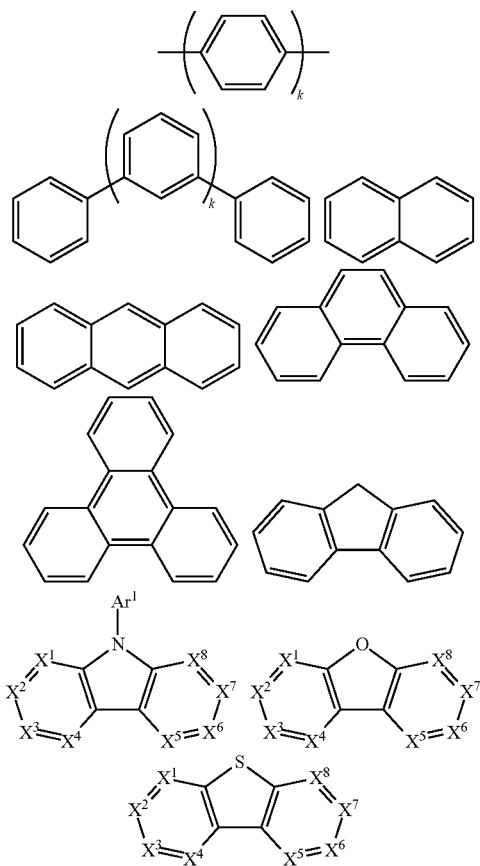

k is an integer from 1 to 20; $X^1$ to $X^8$ is C (including CH) or N; $Ar^1$ has the same group defined above.

Examples of metal complexes used in HIL or HTL include, but not limit to the following general formula:

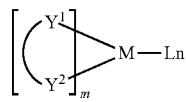

M is a metal, having an atomic weight greater than 40; $(Y^1-Y^2)$ is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, $(Y^1-Y^2)$ is a 2-phenylpyridine derivative.

In another aspect, $(Y^1-Y^2)$ is a carbene ligand.

In another aspect, M is selected from Ir, Pt, Os, and Zn.

In a further aspect, the metal complex has a smallest oxidation potential in solution vs. $Fc^+/Fc$ couple less than about 0.6 V.

In addition to the host materials described above, the device may further comprise other host materials. Examples of such other host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

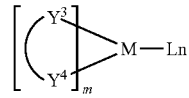

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

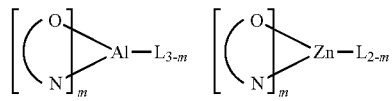

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

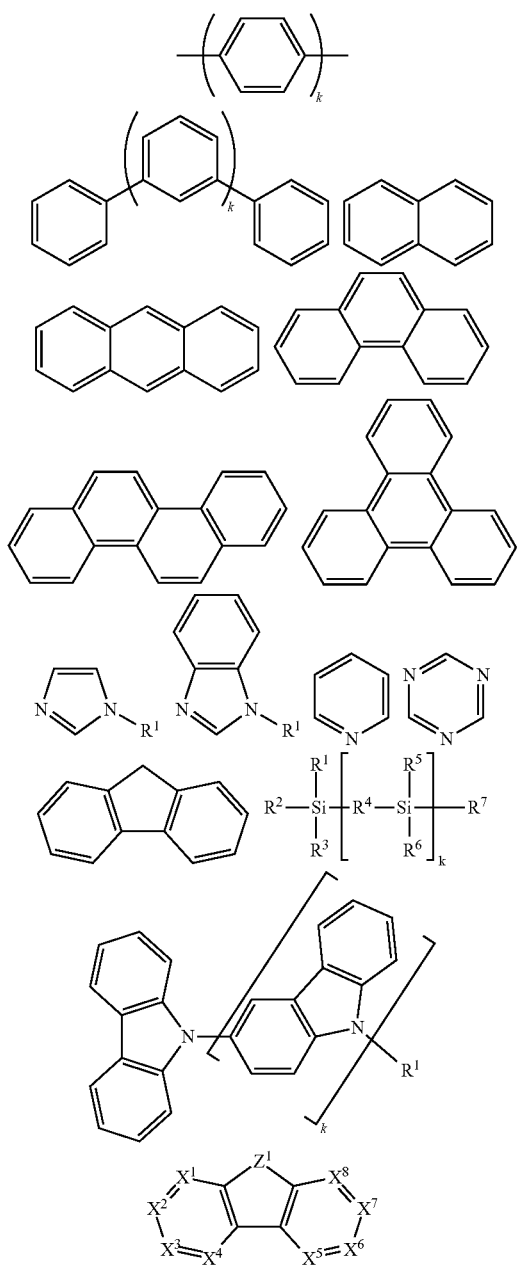

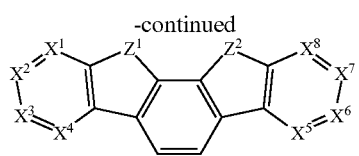

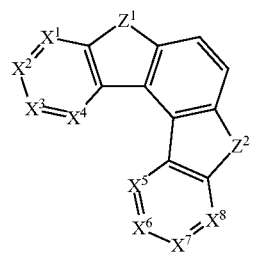

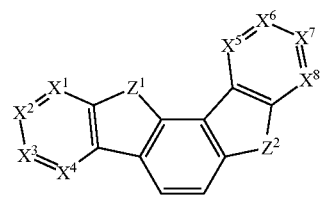

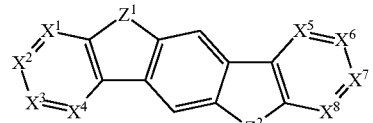

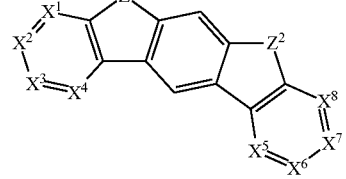

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above; k is an integer from 0 to 20; $X^1$ to $X^8$ are selected from C (including CH) or N; and $Z^1$ and $Z^2$ are selected from $NR^1$, O, or S.

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

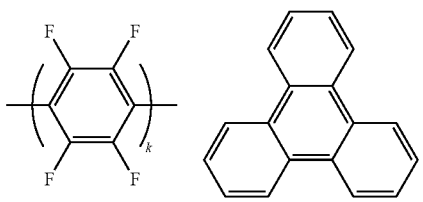

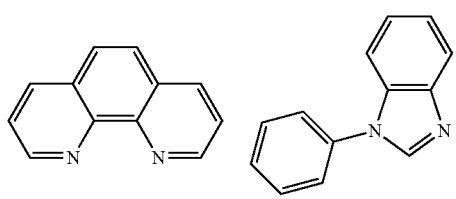

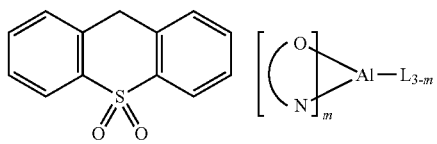

k is an integer from 0 to 20; L is an ancillary ligand, m is an integer from 1 to 3.

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

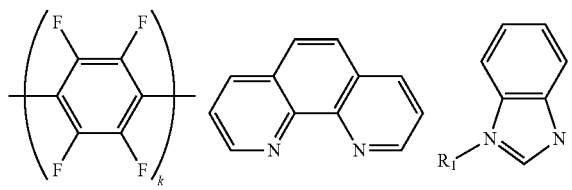

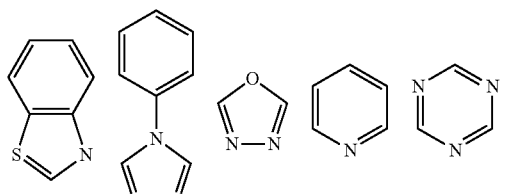

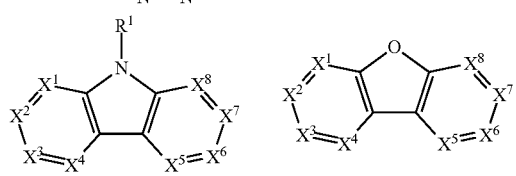

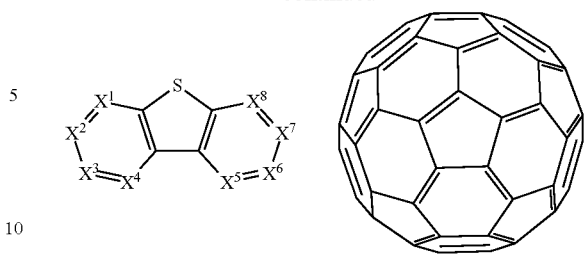

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above; $Ar^1$ to $Ar^3$ has the similar definition as Ar's mentioned above; k is an integer from 0 to 20; $X^1$ to $X^8$ is selected from C (including CH) or N.

In another aspect, the metal complexes used in ETL contains, but not limit to the following general formula:

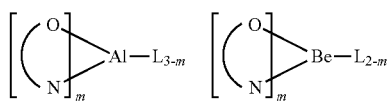

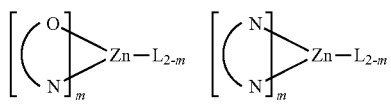

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phthalocyanine and porphryin compounds | 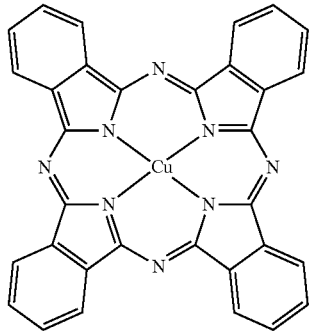 | Appl. Phys. Lett. 69, 2160 (1996) |
| Starburst triarylamines | 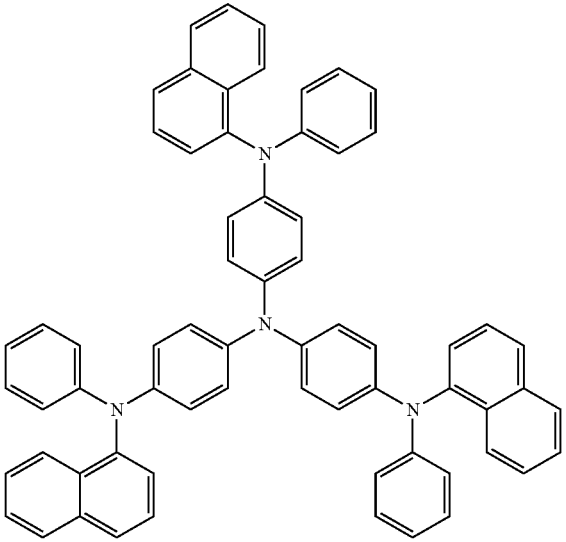 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 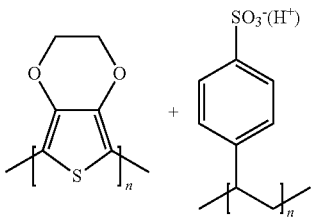 | Synth. Met. 87, 171 (1997) WO2007002683 |
| Phosphonic acid and silane SAMs | 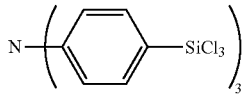 | US20030162053 |
| Triarylamine or polythiophene polymers with conductivity dopants | 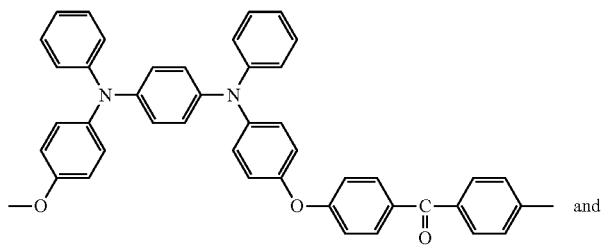 and | EP1725079A1 |

TABLE 1-continued

| MATERIAL | EXAMPLES OF MATERIAL | PUBLICATIONS |
|---|---|---|
| Organic compounds with conductive inorganic compounds, such as molybdenum and tungsten oxides | (structures) + MoO$_x$ | US20050123751 SID Symposium Digest, 37 923 (2006) WO2009018009 |
| n-type semiconducting organic complexes | (structure) | US20020158242 |
| Metal organometallic complexes | (structure) | US20060240279 |

TABLE 1-continued

| MATERIAL | EXAMPLES OF MATERIAL | PUBLICATIONS |
|---|---|---|
| Cross-linkable compounds | | US20080220265 |
| Polythiophene based polymers and copolymers | | WO 2011075644<br>EP2350216 |
| Hole transporting materials | | |
| Triarylamines (e.g., TPD, α-NPD) | | Appl. Phys. Lett. 51, 913 (1987) |
| | | U.S. Pat. No. 5,061,569 |

TABLE 1-continued
| MATERIAL | EXAMPLES OF MATERIAL | PUBLICATIONS |
|---|---|---|
| | 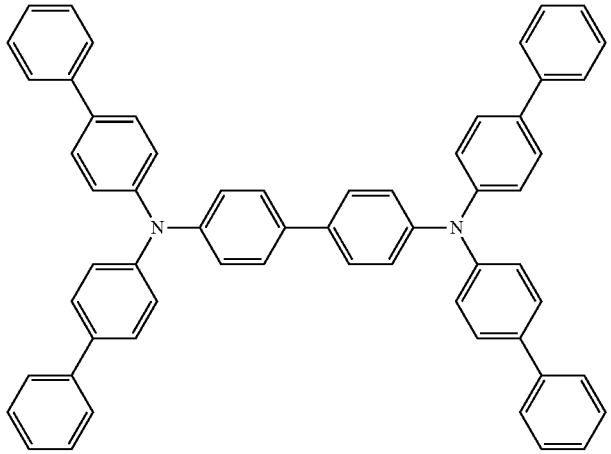 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 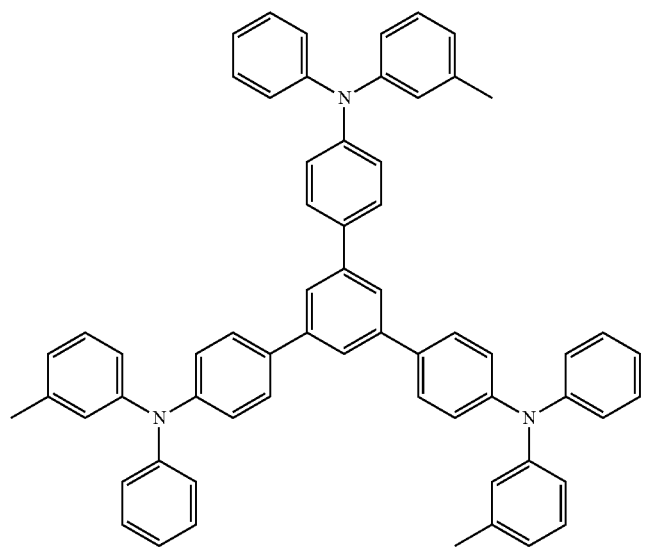 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 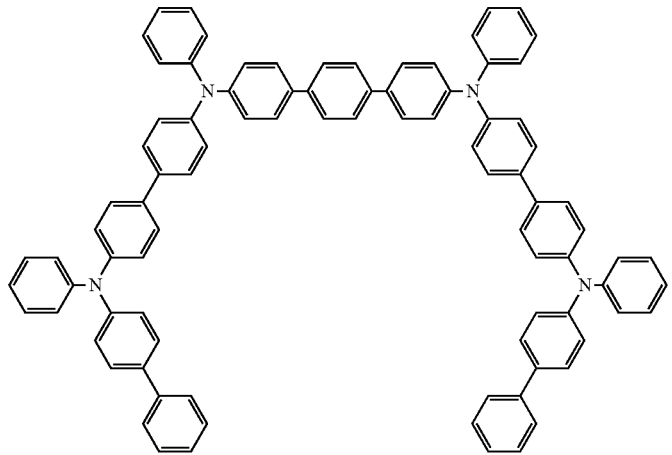 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE 1-continued
| MATERIAL | EXAMPLES OF MATERIAL | PUBLICATIONS |
|---|---|---|
|  | 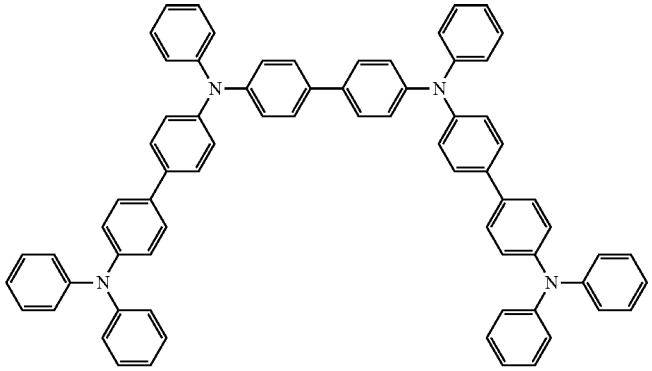 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 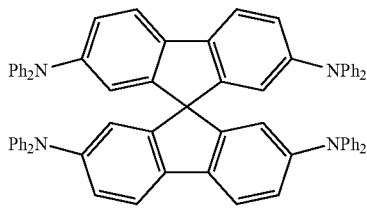 | Synth. Met. 91, 209 (1997) |
| Arylamine carbazole compounds | 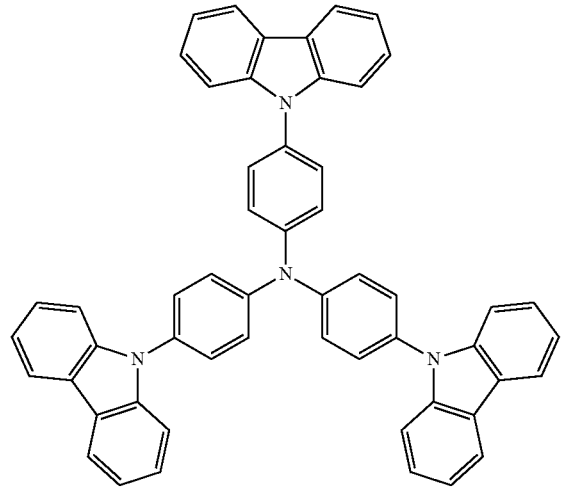 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US2008124572 |
| Triarylamine with (di)benzothiophene/ (di)benzofuran | 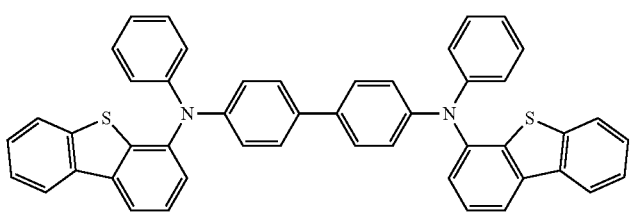 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |

TABLE 1-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE 1-continued

| MATERIAL | EXAMPLES OF MATERIAL | PUBLICATIONS |
| --- | --- | --- |
| Metal 8-hydroxyquinolates (e.g., Alq₃, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE 1-continued

| MATERIAL | EXAMPLES OF MATERIAL | PUBLICATIONS |
|---|---|---|
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20040175553 |
| | | WO2001039234 |
| Aryltriphenylene compounds | | US20060280965 |

TABLE 1-continued
| MATERIAL | EXAMPLES OF MATERIAL | PUBLICATIONS |
|---|---|---|
| | 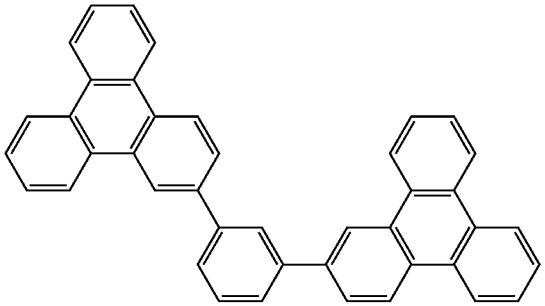 [SMILES: c1cc(-c2ccc3c4ccccc4c4ccccc4c3c2)cc(-c2ccc3c4ccccc4c4ccccc4c3c2)c1] | US20060280965 |
| | 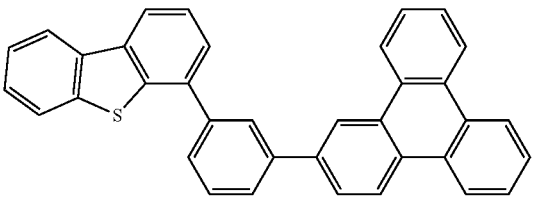 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 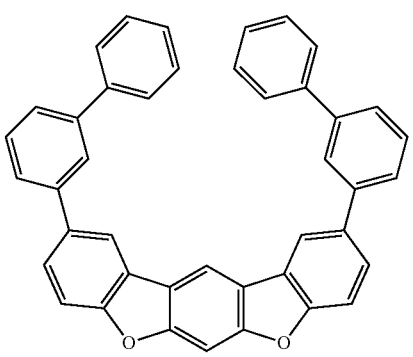 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 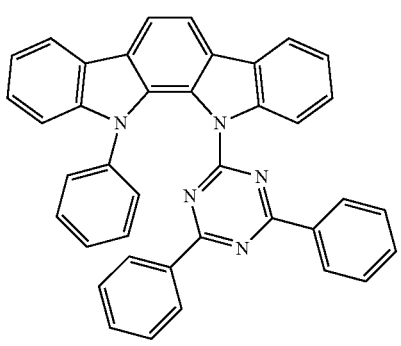 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 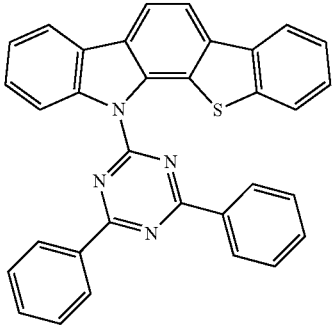 [SMILES: c1ccc(-c2nc(-c3ccccc3)nc(-n3c4ccccc4c4ccc5c6ccccc6sc5c43)n2)cc1] | WO2010107244 |

TABLE 1-continued

| MATERIAL | EXAMPLES OF MATERIAL | PUBLICATIONS |
| --- | --- | --- |
| Aza-carbazole/ DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

TABLE 1-continued

| MATERIAL | EXAMPLES OF MATERIAL | PUBLICATIONS |
|---|---|---|
| | | WO2006132173 |
| | | JP200511610 |
| Spirofluorene-carbazole compounds | | JP2007254297 |
| | | JP2007254297 |
| Indolocabazoles | | WO2007063796 |

TABLE 1-continued

| MATERIAL | EXAMPLES OF MATERIAL | PUBLICATIONS |
|---|---|---|
| | | WO2007063754 |
| 5-member ring electron deficient heterocycles (e.g., triazole, oxidiazole) | | J. Appl. Phys. 90, 5048 (2001) |
| | | WO2004107822 |
| Tetraphenylene complexes | | US20050112407 |
| Metal phenoxypyridine compounds | | WO2005030900 |

TABLE 1-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |

Blue hosts

| | | |
|---|---|---|
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE 1-continued
| MATERIAL | EXAMPLES OF MATERIAL | PUBLICATIONS |
|---|---|---|
| | 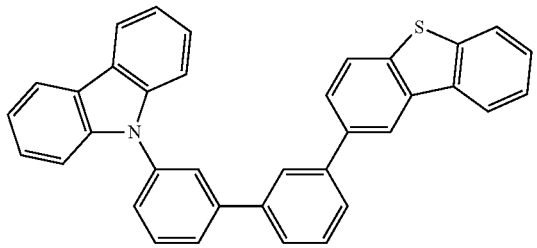 [SMILES: c1cc(-c2cccc(-n3c4ccccc4c4ccccc43)c2)cc(-c2ccc3sc4ccccc4c3c2)c1] | US20090030202, US20090017330 |
| | 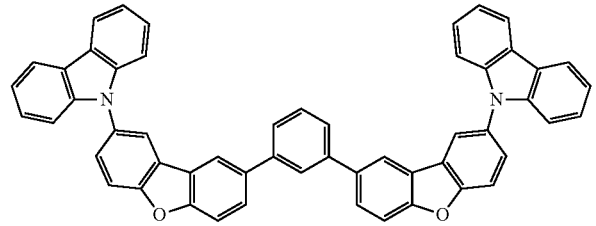 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 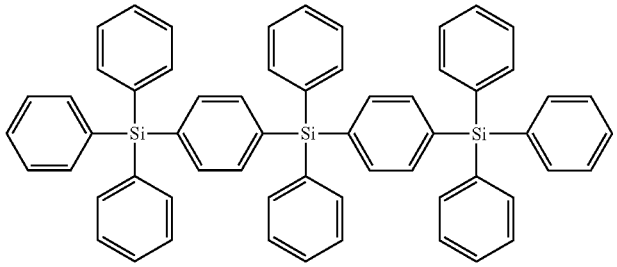 | US20050238919 |
| | 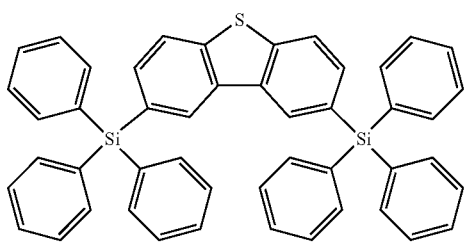 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 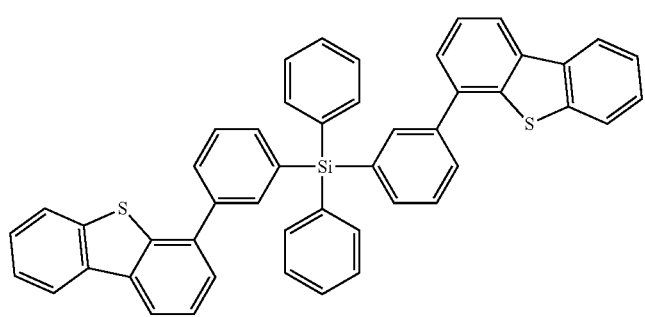 | EP2034538A |
| Aryl benzoyl ester | 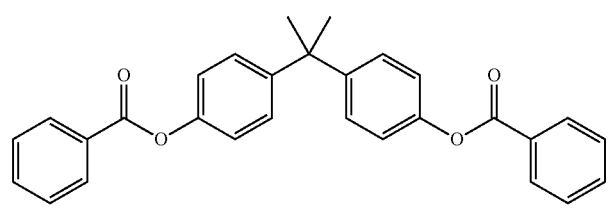 [SMILES: CC(C)(c1ccc(OC(=O)c2ccccc2)cc1)c1ccc(OC(=O)c2ccccc2)cc1] | WO2006100298 |

TABLE 1-continued
| MATERIAL | EXAMPLES OF MATERIAL | PUBLICATIONS |
| --- | --- | --- |
| Carbazole linked by non-conjugated groups | 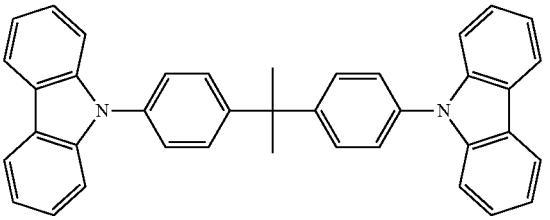 [SMILES: CC(C)(c1ccc(-n2c3ccccc3c3ccccc32)cc1)c1ccc(-n2c3ccccc3c3ccccc32)cc1] | US20040115476 |
| Aza-carbazoles | 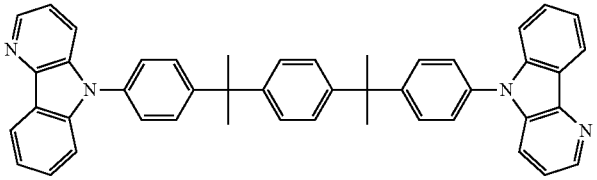 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| High triplet metal organometallic complex | 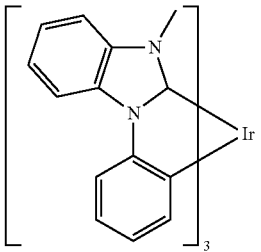 | U.S. Pat. No. 7,154,114 |
Phosphorescent dopants
Red dopants
| Heavy metal porphyrins (e.g., PtOEP) | 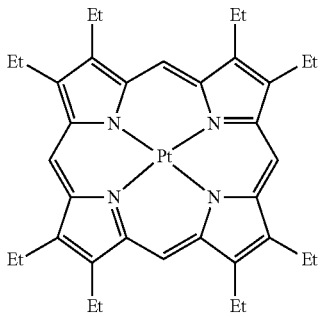 | Nature 395, 151 (1998) |
| --- | --- | --- |
| Iridium(III) organometallic complexes | 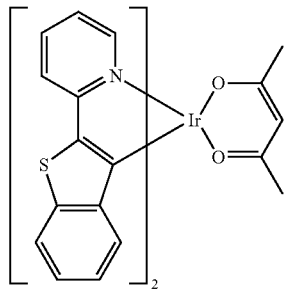 | Appl. Phys. Lett. 78, 1622 (2001) |
| | 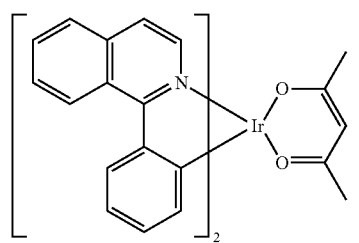 | US2006835469 |

TABLE 1-continued

| MATERIAL | EXAMPLES OF MATERIAL | PUBLICATIONS |
|---|---|---|
| | | US2006835469 |
| | | US20060202194 |
| | | US20060202194 |
| | | US20070087321 |
| | | US20080261076<br>US20100090591 |

TABLE 1-continued

| MATERIAL | EXAMPLES OF MATERIAL | PUBLICATIONS |
|---|---|---|
| | | US20070087321 |
| | | Adv. Mater. 19, 739 (2007) |
| | | WO2009100991 |
| | | WO2008101842 |
| | | U.S. Pat. No. 7,232,618 |

TABLE 1-continued

| MATERIAL | EXAMPLES OF MATERIAL | PUBLICATIONS |
|---|---|---|
| Platinum(II) organometallic complexes | | WO2003040257 |
| | | US20070103060 |
| Osminum(III) complexes | | Chem. Mater. 17, 3532 (2005) |
| Ruthenium(II) complexes | | Adv. Mater. 17, 1059 (2005) |
| Rhenium (I), (II) and (III) complexes | | US20050244673 |

TABLE 1-continued
| MATERIAL | EXAMPLES OF MATERIAL | PUBLICATIONS |
|---|---|---|
| | Green dopants | |
| Iridium(III) organometallic complexes | 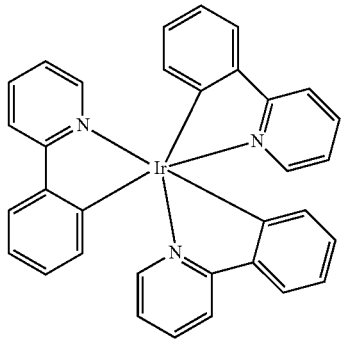<br>and its derivatives | Inorg. Chem. 40, 1704 (2001) |
| | 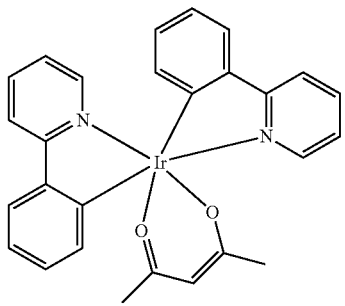 | US20020034656 |
| | 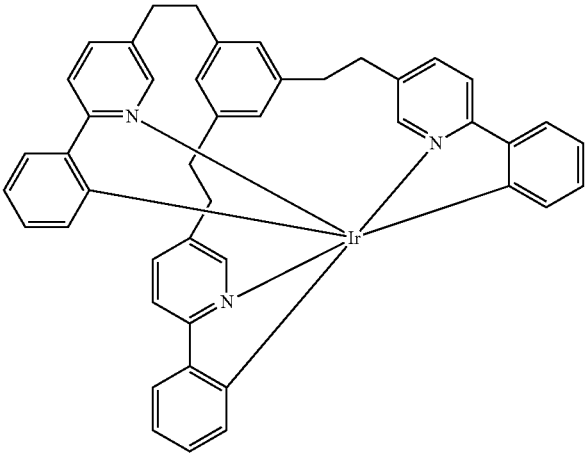 | U.S. Pat. No. 7,332,232 |
| | 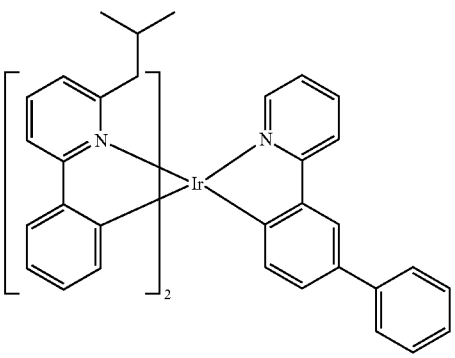 | US20090108737 |

TABLE 1-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE 1-continued

| MATERIAL | EXAMPLES OF MATERIAL | PUBLICATIONS |
|---|---|---|
| | | US20100244004 |
| | | U.S. Pat. No. 6,687,266 |
| | | Chem. Mater. 16, 2480 (2004) |
| | | US20070190359 |
| | | US 20060008670<br>JP2007123392 |

TABLE 1-continued

| MATERIAL | EXAMPLES OF MATERIAL | PUBLICATIONS |
|---|---|---|
| | | WO2010086089, WO2011044988 |
| | | Adv. Mater. 16, 2003 (2004) |
| | | Angew. Chem. Int. Ed. 2006, 45, 7800 |
| | | WO2009050290 |
| | | US20090165846 |
| | | US20080015355 |

TABLE 1-continued

| MATERIAL | EXAMPLES OF MATERIAL | PUBLICATIONS |
| --- | --- | --- |
| | | US20010015432 |
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |

TABLE 1-continued
| MATERIAL | EXAMPLES OF MATERIAL | PUBLICATIONS |
|---|---|---|
| | 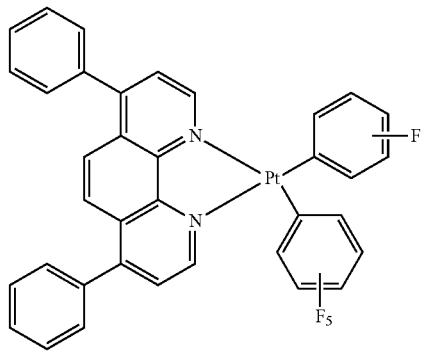 | Chem. Lett. 34, 592 (2005) |
| | 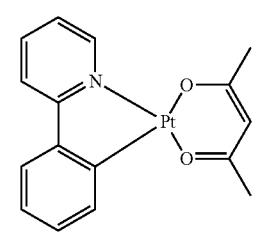 | WO2002015645 |
| | 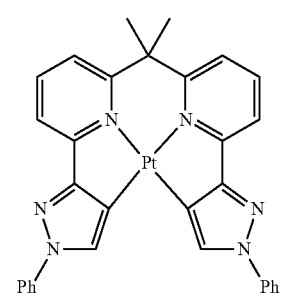 | US20060263635 |
| | 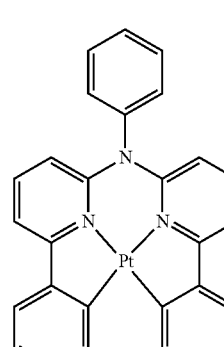 | US20060182992<br>US20070103060 |

TABLE 1-continued
| MATERIAL | EXAMPLES OF MATERIAL | PUBLICATIONS |
|---|---|---|
| Cu complexes | 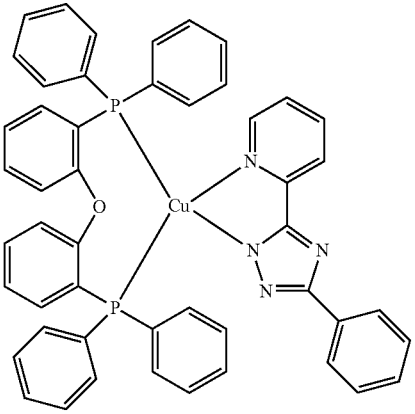 | WO2009000673 |
| | 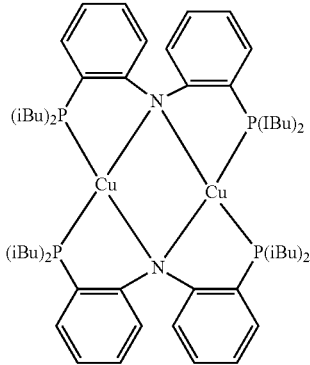 | US20070111026 |
| Gold complexes | 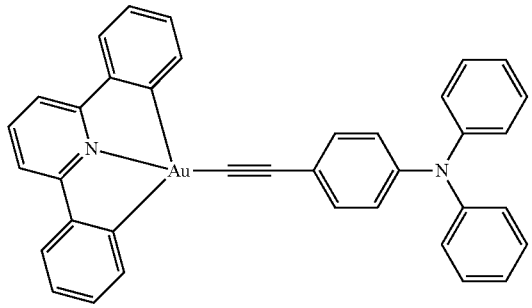 | Chem. Commun. 2906 (2005) |
| Rhenium(III) complexes | 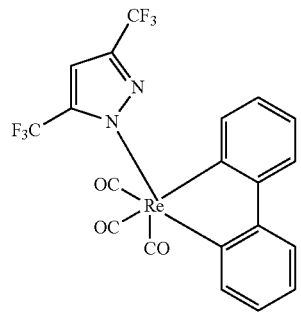 | Inorg. Chem. 42, 1248 (2003) |

TABLE 1-continued

| MATERIAL | EXAMPLES OF MATERIAL | PUBLICATIONS |
|---|---|---|
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE 1-continued
| MATERIAL | EXAMPLES OF MATERIAL | PUBLICATIONS |
|---|---|---|
| Blue dopants | | |
| Iridium(III) organometallic complexes | 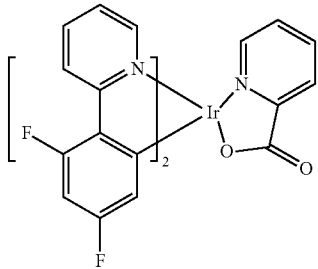 | WO2002002714 |
| | 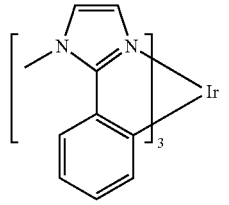 | WO2006009024 |
| | 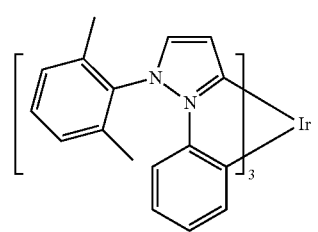 | US20060251923<br>US20110057559<br>US20110204333 |
| | 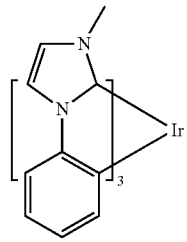 | U.S. Pat. No. 7,393,599,<br>WO2006056418,<br>US20050260441,<br>WO2005019373 |
| | 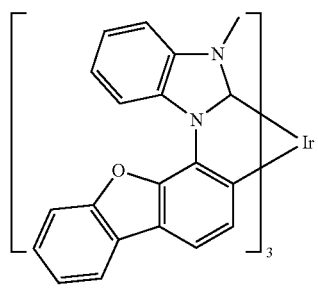 | U.S. Pat. No. 7,534,505 |
| | 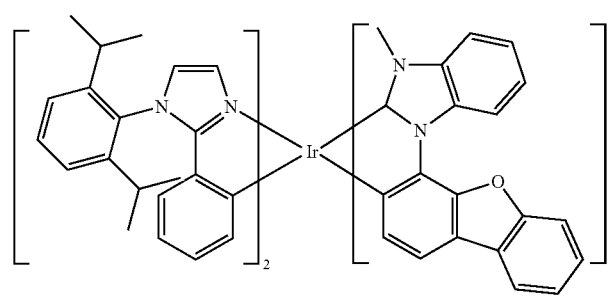 | WO2011051404 |

TABLE 1-continued

| MATERIAL | EXAMPLES OF MATERIAL | PUBLICATIONS |
|---|---|---|
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 1 (2008) |

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE 1-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 1-continued

| MATERIAL | EXAMPLES OF MATERIAL | PUBLICATIONS |
|---|---|---|
| Pt tetradentate complexes with at least one metal-carbene bond | 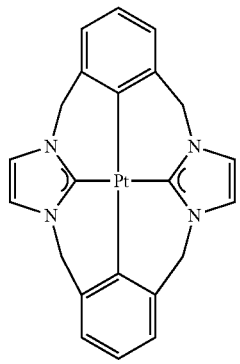 | U.S. Pat. No. 7,655,323 |
| Exciton/hole blocking layer materials | | |
| Bathocuprine compounds (e.g., BCP, BPhen) | 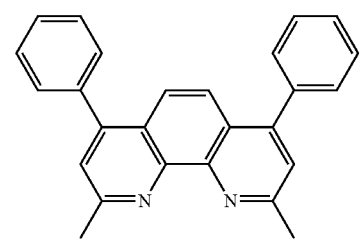 [SMILES: Cc1cc(-c2ccccc2)c2ccc3c(-c4ccccc4)cc(C)nc3c2n1] | Appl. Phys. Lett. 75, 4 (1999) |
| | 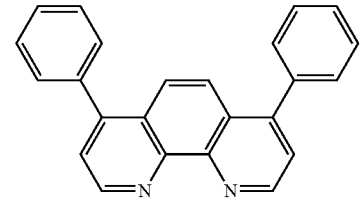 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 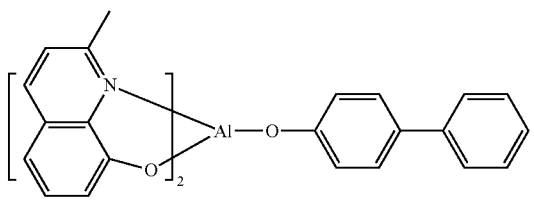 | Appl. Phys. Lett. 81, 162 (2002) |
| 5-member ring electron deficient heterocycles such as triazole, oxadiazole, imidazole, benzoimidazole | 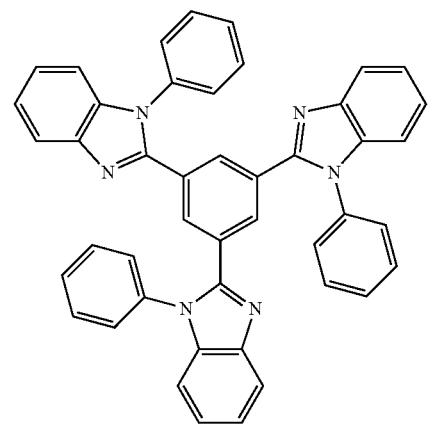 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 1-continued
| MATERIAL | EXAMPLES OF MATERIAL | PUBLICATIONS |
|---|---|---|
| Triphenylene compounds | 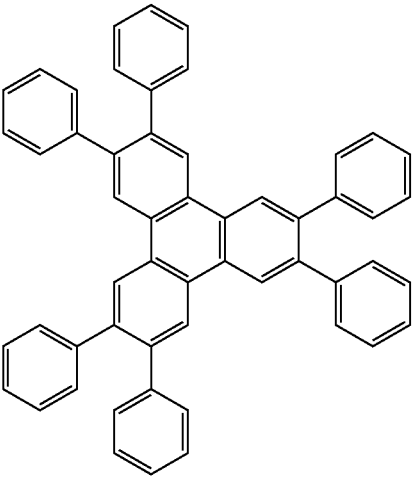 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 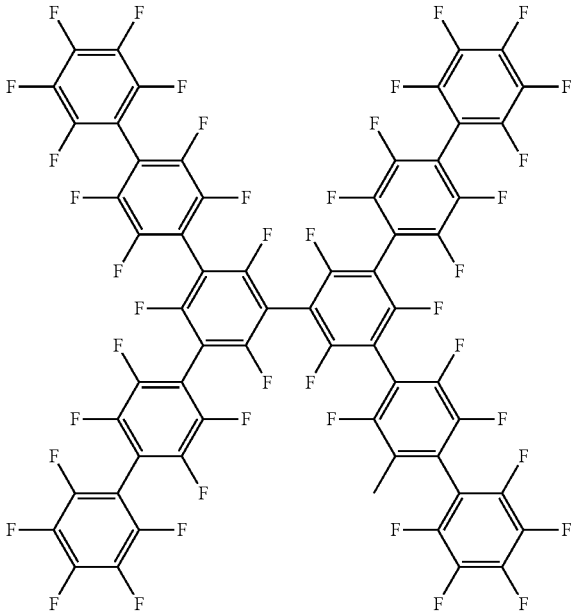 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 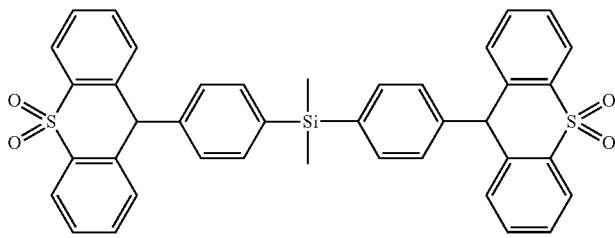 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 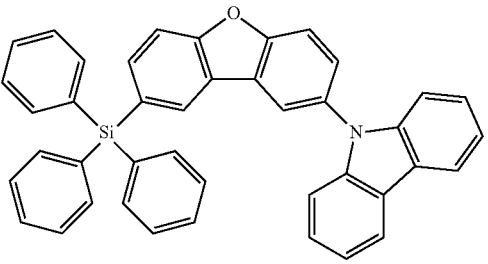 [SMILES: c1ccc([Si](c2ccccc2)(c2ccccc2)c2ccc3oc4ccc(-n5c6ccccc6c6ccccc65)cc4c3c2)cc1] | WO2010079051 |

TABLE 1-continued
| MATERIAL | EXAMPLES OF MATERIAL | PUBLICATIONS |
|---|---|---|
| Aza-carbazoles | 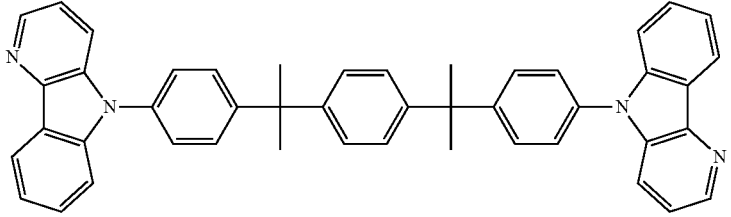 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 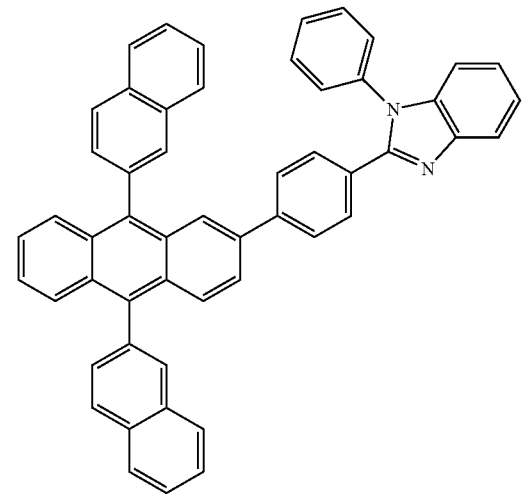 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 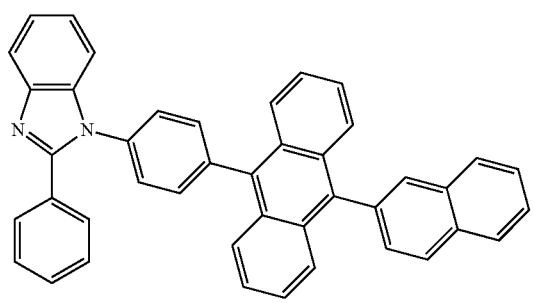 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 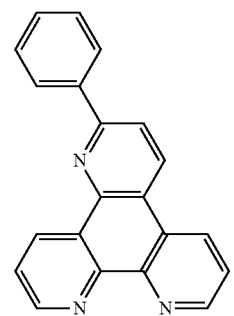 [SMILES: c1ccc(-c2ccc3c4cccnc4c4ncccc4c3n2)cc1] | US20090115316 |
| Anthracene-benzothiazole compounds | 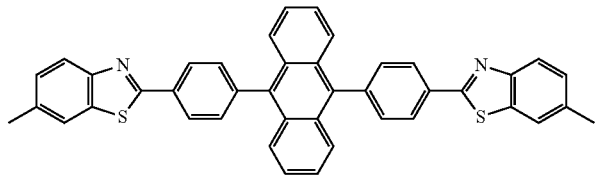 | Appl. Phys. Lett. 89, 063504 (2006) |

TABLE 1-continued

| MATERIAL | EXAMPLES OF MATERIAL | PUBLICATIONS |
| --- | --- | --- |
| Metal 8-hydroxyquinolates (e.g., Alq$_3$, Zrq$_4$) | 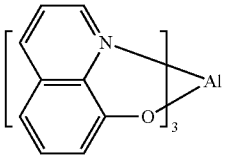 | Appl. Phys. Lett. 51, 913 (1987)<br>U.S. Pat. No. 7,230,107 |
| Metal hydroxy-benoquinolates | 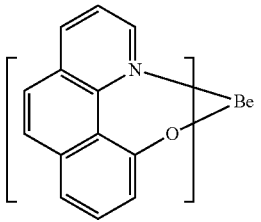 | Chem. Lett. 5, 905 (1993) |
| Bathocuprine compounds such as BCP, BPhen, etc | 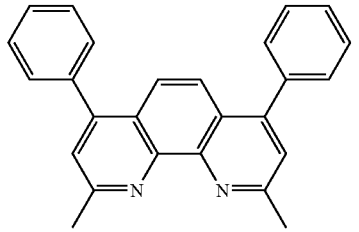 [SMILES: Cc1cc(-c2ccccc2)c2ccc3c(-c4ccccc4)cc(C)nc3c2n1] | Appl. Phys. Lett. 91, 263503 (2007) |
|  | 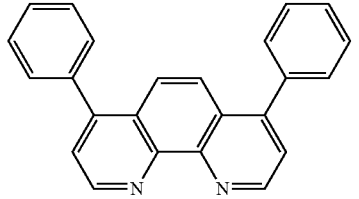 [SMILES: c1ccc(-c2ccnc3c2ccc2c(-c4ccccc4)ccnc23)cc1] | Appl. Phys. Lett. 79, 449 (2001) |
| 5-member ring electron deficient heterocycles (e.g., triazole, oxadiazole, imidazole, benzoimidazole) | 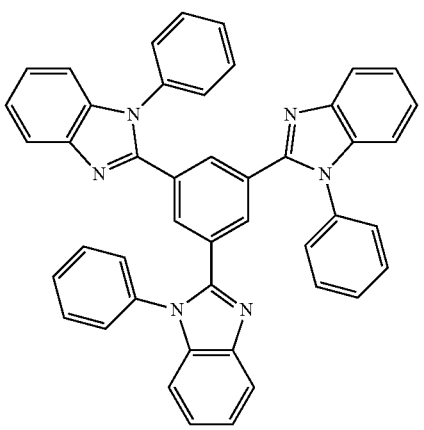 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
|  | 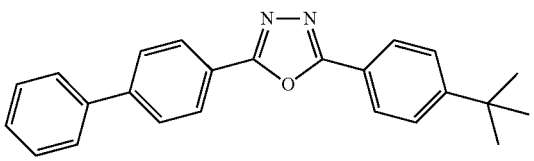 [SMILES: CC(C)(C)c1ccc(-c2nnc(-c3ccc(-c4ccccc4)cc3)o2)cc1] | Appl. Phys. Lett. 55, 1489 (1989) |

TABLE 1-continued

| MATERIAL | EXAMPLES OF MATERIAL | PUBLICATIONS |
| --- | --- | --- |
| | [triazole structure] | Jpn. J. Apply. Phys. 32, L917 (1993) |
| Silole compounds | [silole structure] | Org. Electron. 4, 113 (2003) |
| Arylborane compounds | [arylborane structure] | J. Am. Chem. Soc. 120, 9714 (1998) |
| Fluorinated aromatic compounds | [perfluorinated oligophenyl structure] | J. Am. Chem. Soc. 122, 1832 (2000) |
| Fullerene (e.g., C60) | [C60 structure] | US20090101870 |
| Triazine complexes | [fluorinated triazine structure] | US20040036077 |

TABLE 1-continued

| MATERIAL | EXAMPLES OF MATERIAL | PUBLICATIONS |
|---|---|---|
| Zn (N^N) complexes | 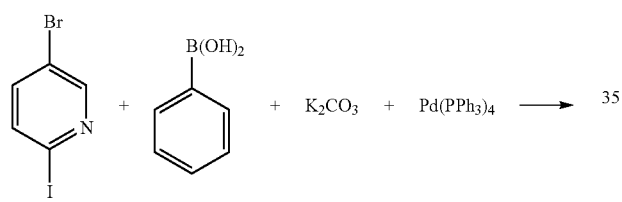 | U.S. Pat. No. 6,528,187 |

EXPERIMENTAL

Compound Examples

Some of the heteroleptic complexes were synthesized as follows.

Synthesis of Compound 1.

Preparation of 5-bromo-2-phenylpyridine

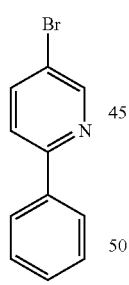

5-bromo-2-iodopyridine (15 g, 52.8 mmol), phenylboronic acid (6.44 g, 52.8 mmol), tetrakis(triphenylphosphine) palladium(0) (0.611 g, 0.528 mmol), and potassium carbonate (83 g, 598 mmol) were added to 260 mL 4:1 DME and water. The reaction mixture was degassed with bubbled nitrogen gas for 30 min and was stirred at reflux for 18 h in an inert environment. The cooled reaction mixture was poured over water and partitioned between brine and ethyl acetate. Organic layers were combined, and were dried over $MgSO_4$ and solvents were removed under reduced pressure. The crude product was purified by column chromatography over silica gel using 5-15% DCM/hexanes as eluent. 4.18 g (33.8%) of 5-bromo-2-phenylpyridine was isolated as a white solid.

Preparation of N,N, 6-triphenylpyridine-3-amine

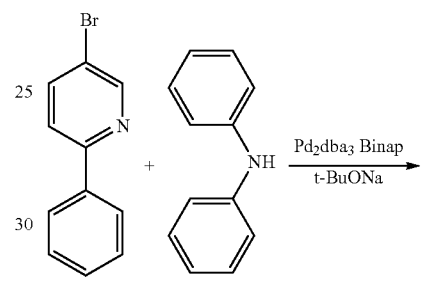

5-Bromo-2-phenylpyridine (7.0 g, 29.9 mmol) and diphenylamine (6.07 g, 35.9 mmol) were dissolved in 300 ml m-xylene in a 500 ml 3-neck round bottom flask, then purged nitrogen directly into the clear solution for 30 minutes. Sodium t-butoxide (5.75 g, 59.8 mmol), binap (1.49 g, 2.39 mmol), and $Pd_2dba_3$ (1.10 g, 1.20 mmol) were added to the solution in that order. The reaction was heated to a vigorous reflux under nitrogen overnight. The dark brown reaction was then transferred to a separatory funnel with ethyl acetate and water. The aqueous portion was extracted with ethyl acetate twice. The combined organic layers were dried with sodium sulfate, filtered and rotovaped down to a brown solid. The crude product was adsorbed onto Celite and purified with silica gel column chromatography using 25/75 DCM/hexane to 100% DCM gradient solvent system. The major product spot was recovered and evaporated to beige solid. (8.0 g).

Preparation of Compound 1.

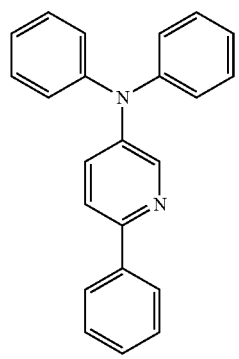

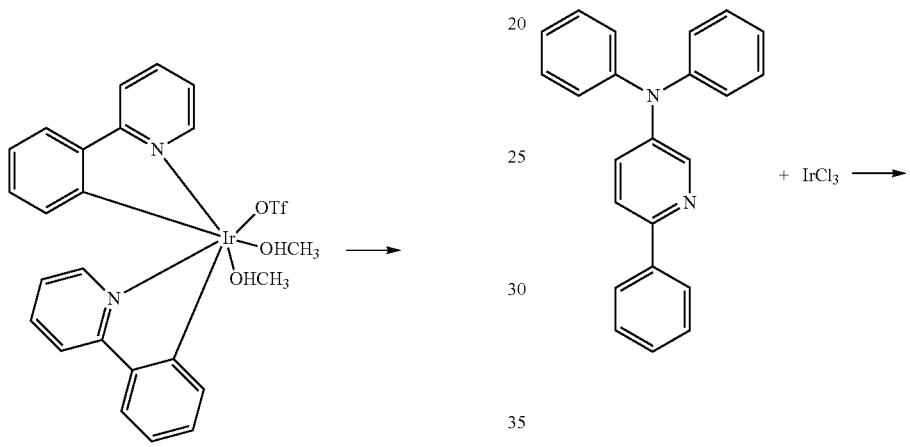

N,N, 6-Triphenylpyridin-3-amine (6.37 g, 19.75 mmol), phenylpyridine iridium triflate intermediate (4.7 g, 6.58 mmol) and 130 mL ethanol were combined into a 250 ml single neck round bottom flask. A condenser was attached then the system was evacuated and purged with nitrogen three times. The suspension was heated to a vigorous reflux in an oil bath overnight The reaction was cooled to room temperature, added Celite then filtered off a bright yellow suspension using a Celite pad in a sintered filter funnel. The solid was washed well with ethanol. The crude product was recovered by washing the Celite with DCM, then evaporating the filtrate down to a yellow solid. The sample was purified using silica gel column chromatography with 50/50 DCM/Hexane solvent system. The desired fractions were combined and rotovaped down to an orange yellow solid. (4.1 g).

The sample was refluxed in 150 ml toluene in a 250 ml single neck round bottom flask under nitrogen using an oil bath for 4 hours. The suspension was removed and allowed to cool to room temperature for one hour then filtered through filter paper in a Buchner funnel. The solid was further dried in a vacuum oven set at 60° C. overnight giving Compound 1 (2.70 g, 42.5% yield).

Synthesis of Compound D.
Preparation of Iridium Dimer.

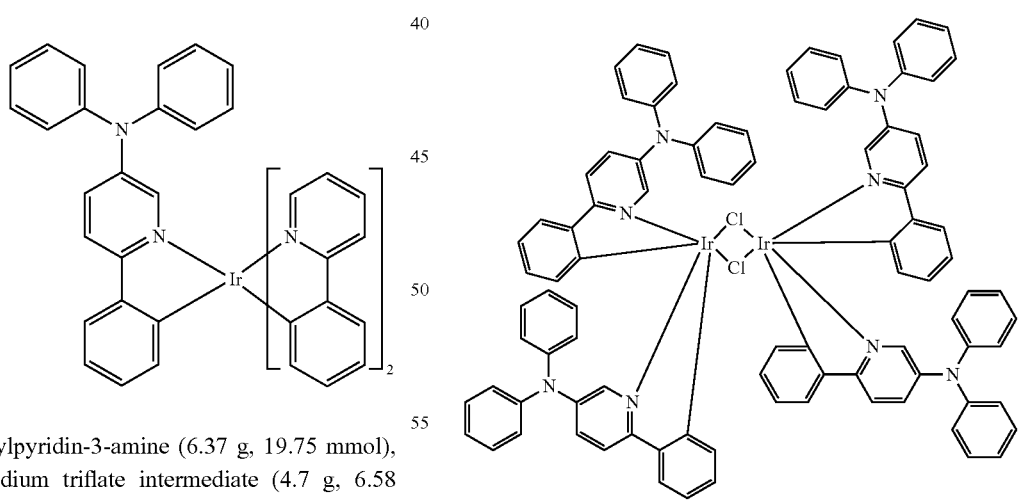

N,N,6-triphenylpyridin-3-amine (2.27 g, 7.03 mmol) and iridium(III) chloride (1 g, 3.35 mmol) were mixed together in 40 mL of 3:1 mixture of ethoxyethanol and water. The reaction mixture was degassed by bubbling nitrogen gas and it was stirred at reflux under nitrogen for 18 h. The reaction mixture was cooled to room temperature and diluted with 50 mL methanol. The solid precipitates were collected and used without further purification.

Preparation of Iridium Triflate Intermediate.

AgOTf +
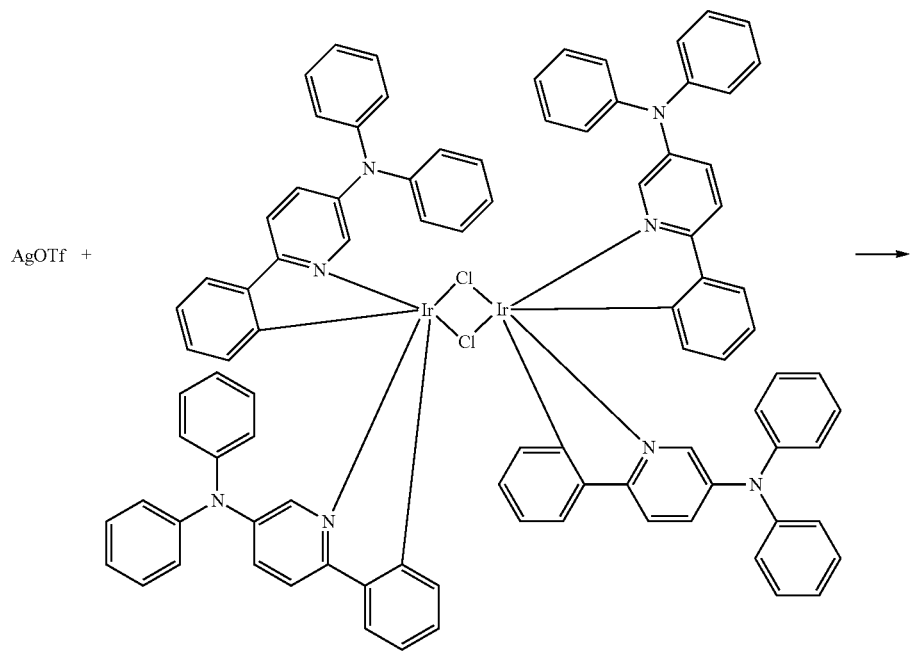
→

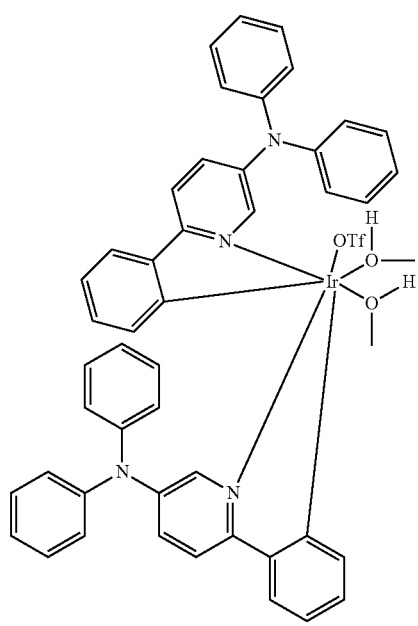

Silvertriflate (0.597 g, 2.325 mmol) was dissolved in 8 mL of methanol and Iridium dimer (1.84 g, 1.057 mmol) was added to it followed by 15 mL dichloromethane. The reaction mixture was heated to reflux under nitrogen in a dark area for 18 h. The cooled reaction mixture was filtered through a Celite plug. Solvents were removed from the filtrate and the isolated solid was used for next step without further purification.

Preparation of Compound D.

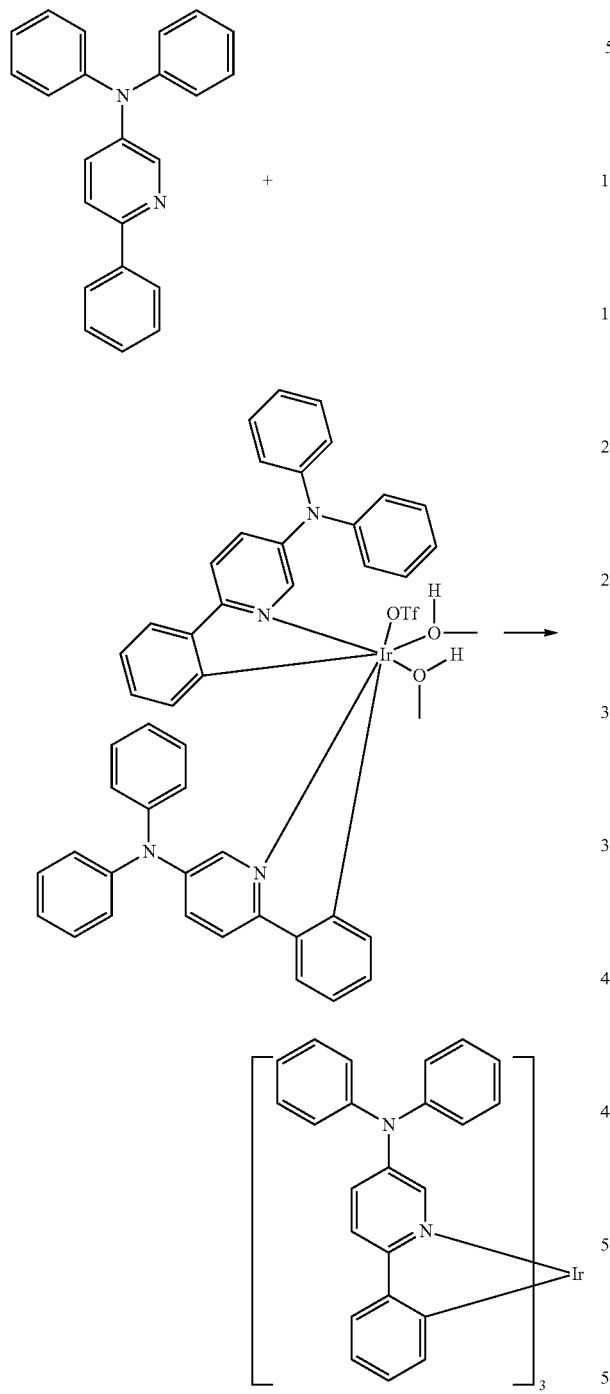

N,N,6-triphenylpyridin-3-amine (1.846 g, 5.72 mmol) and Iridium triflate intermediate (2 g, 1.908 mmol) were added to 60 mL of ethanol and this was stirred at reflux for 18 h. The cooled mixture was then filtered through Celite and the cake was washed with ethanol. The filter funnel was then placed on a separated funnel and the product was extracted with dichloromethane. Evaporation of the filtrate gave 2.0 grams of crude solid which was purified over silica gel using 1:1 to 7:3 dichloromethane/hexanes as eluent to obtain 1.45 grams (66%) of Compound D.

Synthesis of Compound 2.

Preparation of 5-bromo-4-methyl-2-phenylpyridine

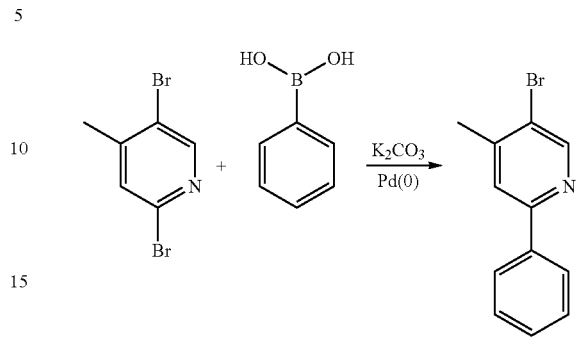

2,5-Dibromo-4-methylpyridine (25 g, 100 mmol) and phenylboronic acid (12.15 g, 100 mmol) were added to a 1 L flask. DME (250 mL), water (100 mL) and potassium carbonate (27.5 grams, 200 mmol) were then added. This was degassed before addition of tetrakis(triphenylphosphine)palladium(0) (5.76 grams, 5%). The reaction was stirred at reflux overnight.

The mixture was filtered through Celite and the cake was washed with ethyl acetate. The filtrate was then diluted with more ethyl acetate and brine. Layers were separated. The organic layer was concentrated and chromatographed (silica gel) elution with 0-15% DCM in hexane followed by 10% ethyl acetate in hexane gave 18.9 grams (77%) of the product as an oil.

Preparation of 4-methyl-N,N,6-triphenylpyridin-3-amine

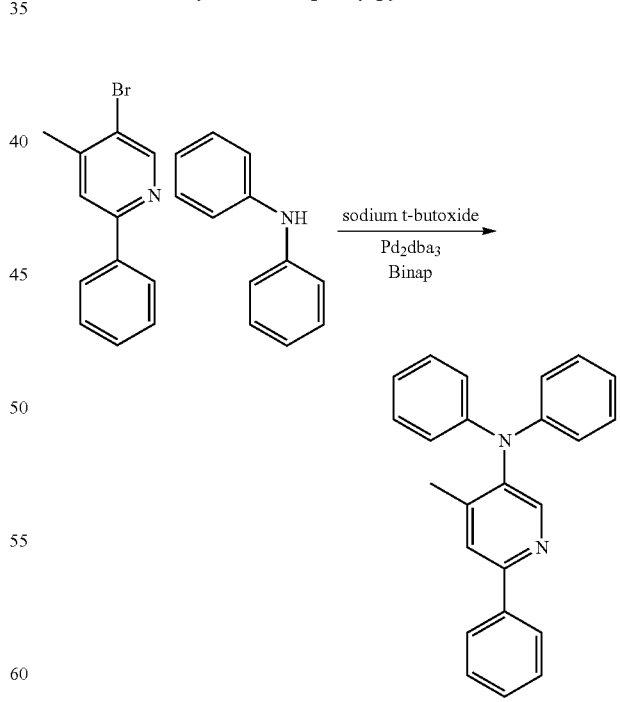

5-Bromo-4-methyl-2-phenylpyridine (7.44 g, 30.0 mmol) was added to a 500 mL 3 necked flask. The reaction mixture was diluted with Xylene (250 ml). Diphenylamine (6.09 g, 36.0 mmol) was added and the mix was degassed. Sodium t-butoxide (5.77 g, 60.0 mmol) and 2,2'-bis(diphenylphosphino)-1,1'-binaphthalene (binap) (1.494 g, 2.400 mmol) and Pd₂dba₃ (1.099 g, 1.200 mmol) were added. This was stirred at reflux for 18H. The crude mixture was filtered through Celite and chromatographed using a mobile phase of first 1:1 DCM-hexane then 5-10% ethyl acetate in hexane to afford 7.68 grams (76%) of product as a pale yellow foam.

Preparation of Compound 2.

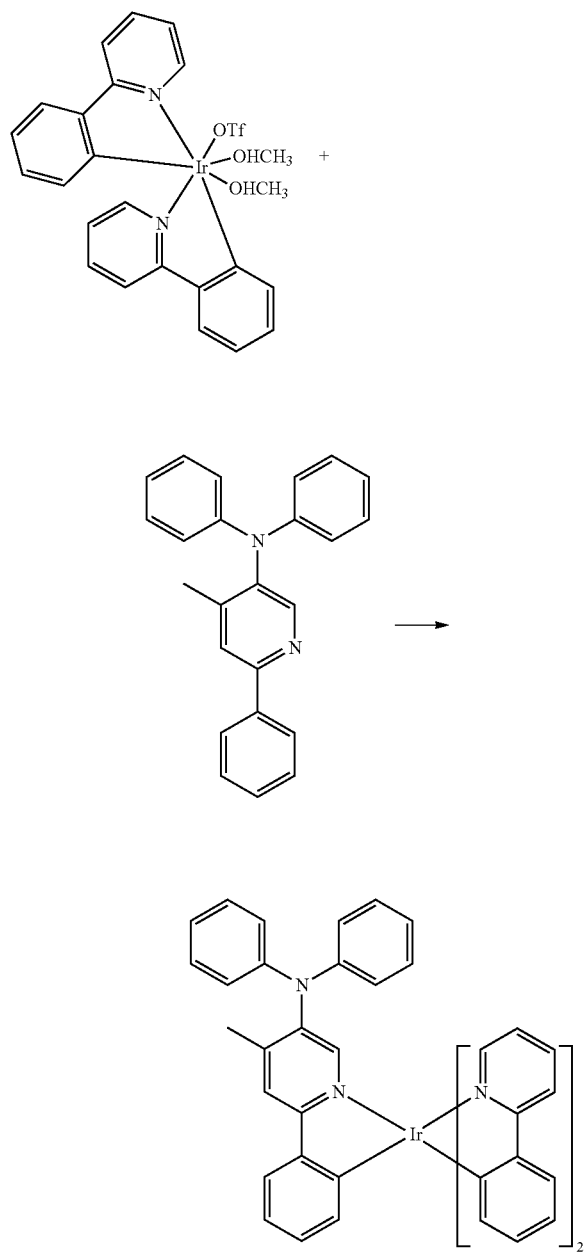

4-Methyl-N,N,6-triphenylpyridin-3-amine (7.65 g, 22.74 mmol) and phenylpyridine Iridium triflate intermediate (5.41 g, 7.58 mmol) were added to a 500 mL round bottom flask. The reaction mixture was diluted with Ethanol (120 ml) and the reaction was stirred at reflux for 23H. The mixture was filtered through Celite and washed with ethanol. The filter funnel was moved to different filter flask and washed with DCM. The filtrate was evaporated and adsorbed onto Celite and chromatographed eluting with 1:1 DCM-hexane to get 5.65 grams of Compound 2.

Synthesis of Compound 3.

Preparation of 9-(6-phenylpyridin-3-yl)-9H-carbazole

5-Bromo-2-phenylpyridine (8.0 g, 34.2 mmol) and 9H-carbazole (6.86 g, 41.0 mmol) were dissolved in 300 ml m-xylene in a 1000 ml 3-neck round bottom flask, then purged nitrogen directly into the reaction for 30 minutes. Sodium tert-butoxide (6.57 g, 68.3 mmol), 2,2'-bis(diphenylphosphino)-1,1'-binaphthalene (1.70 g, 2.73 mmol), and Pd₂dba₃ (1.25 g, 1.37 mmol) were added to the reaction in that order. The reaction was heated to a vigorous reflux under nitrogen overnight.

The dark brown reaction was transferred to a separatory funnel with ethyl acetate and water. Added brine solution, then the aqueous portion was extracted with ethyl acetate twice. The combined organic portions were washed once with saturated brine solution. The organic portion was dried with sodium sulfate, filtered and rotovaped down to a reddish-brown solid. The crude product was adsorbed onto Celite and purified with a silica gel column using 90/10 then 85/15 Ethyl acetate/hexane solvent system. The appropriate fractions were evaporated down to a brown solid. (11.5 g) The sample was recrystallized by refluxing it in (600 ml) hexane then adding ethyl acetate to get a solution. The solution was allowed to cool then the precipitate was filtered off using a sintered frit funnel and washed with hexane to obtain the desired product (6.3 grams) as an off white solid.

Preparation of Compound 3.

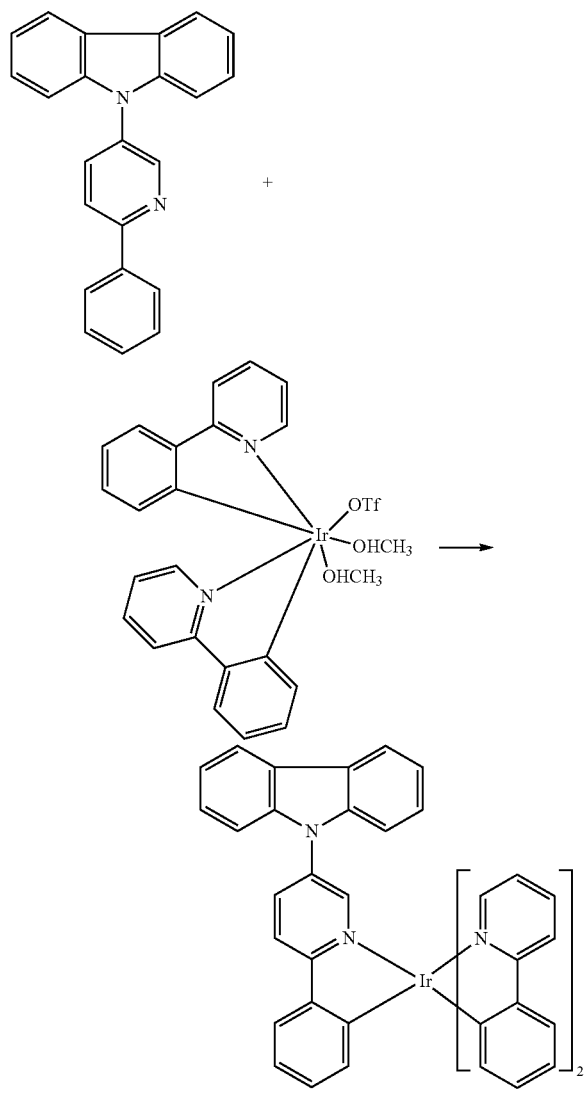

9-(6-Phenylpyridin-3-yl)-9H-carbazole (5.52 g, 17.2 mmol), phenylpyridine iridium triflate intermediate (4.1 g, 5.74 mmol) and 120 mL ethanol were combined into a 250 ml single neck round bottom flask. A condenser was attached then the system was evacuated and purged three times with nitrogen. The suspension was heated to a vigorous reflux in an oil bath for forty hours. The reaction was cooled to room temperature. Celite was added to the reaction which was filtered giving a bright yellow solid. The filter cake was washed well with ethanol. The solid was removed from the Celite by dissolving it in dichloromethane, then evaporating the solvent to a yellow solid. The sample was adsorbed onto Celite then purified with a silica gel column eluted with 75/25, 50/50, then 25/75 Hexane/DCM solvent system to achieve complete separation of the two spots. Fractions containing the product were combined and rotovaped down to get an orange-yellow solid. This was further purified using reverse phase chromatography on a C18 column eluted with 95% acetonitrile in water. Fractions containing product were combined and evaporated to an orange-yellow solid of Compound 3 (1.35 g).

Synthesis of Compound 4.

Preparation of 5-iodo-4-methyl-2-phenylpyridine

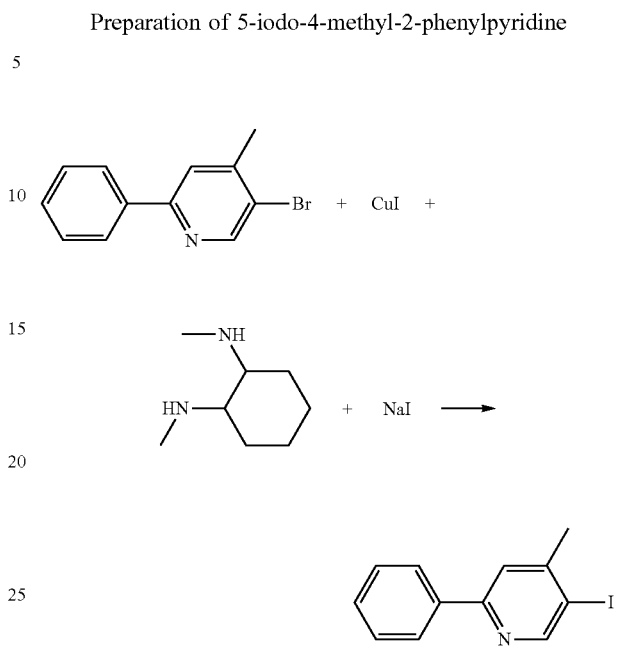

5-Bromo-4-methyl-2-phenylpyridine (7.01 g, 28.3 mmol), copper(I) iodide (1.076 g, 5.65 mmol), N1,N2-dimethylcyclohexane-1,2-diamine (1.782 ml, 11.30 mmol) and sodium iodide (12.70 g, 85 mmol) were added to 105 mL dioxane to give a green suspension which was degassed for 30 minutes by bubbling nitrogen gas. The reaction mixture was heated to reflux for 20H. The reaction mixture was cooled to room temperature and partitioned between saturated ammonium chloride solution and ethyl acetate. The organic layers were combined, dried over Magnesium sulfate and the solvents were removed under reduced pressure to give a brown crude oil which was purified by silica gel column chromatography using 10% ethyl acetate in hexanes. 5-iodo-4-methyl-2-phenylpyridine (7.23 g, 87% yield) was isolated as colorless oil.

Preparation of 9-(4-methyl-6-phenylpyridin-3-yl)-9'-1-carbazole

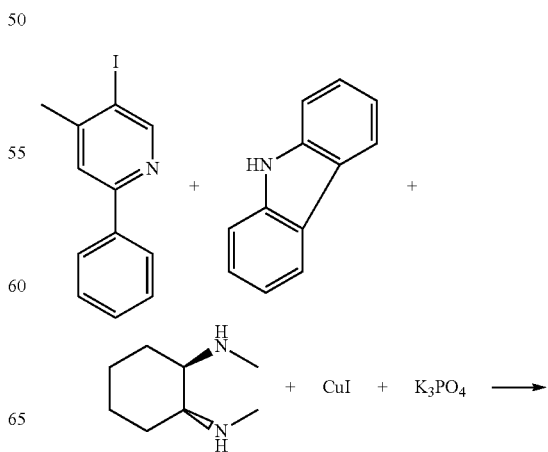

-continued

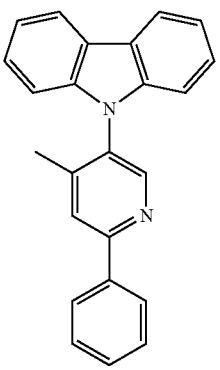

5-Iodo-4-methyl-2-phenylpyridine (4 g, 13.55 mmol), 9H-carbazole (9.07 g, 54.2 mmol), (1R,2S)—N1,N2-dimethylcyclohexane-1,2-diamine (0.855 ml, 5.42 mmol), copper(I) iodide (0.516 g, 2.71 mmol) and potassium phosphate (14.39 g, 67.8 mmol) were added to 40 mL dioxane and degassed for 30 minutes. The reaction mixture was stirred at reflux for 7 days. The mixture was cooled to room temperature and dioxane was removed under reduced pressure. The crude material was chromatographed over silica gel using 5-10% ethyl acetate/hexanes as eluent. The isolated material was recrystallized from boiling hexanes and DCM. 9-(4-methyl-6-phenylpyridin-3-yl)-9H-carbazole (1.4 g, 31% yield) was isolated as white crystalline material.

Preparation of Compound 4 and Compound 5

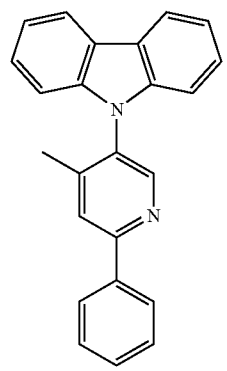

+

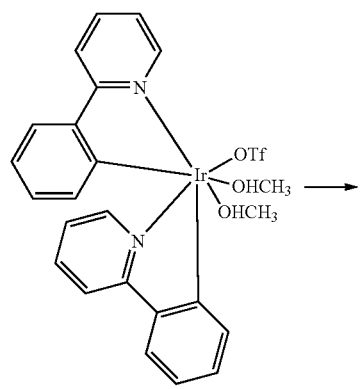

-continued

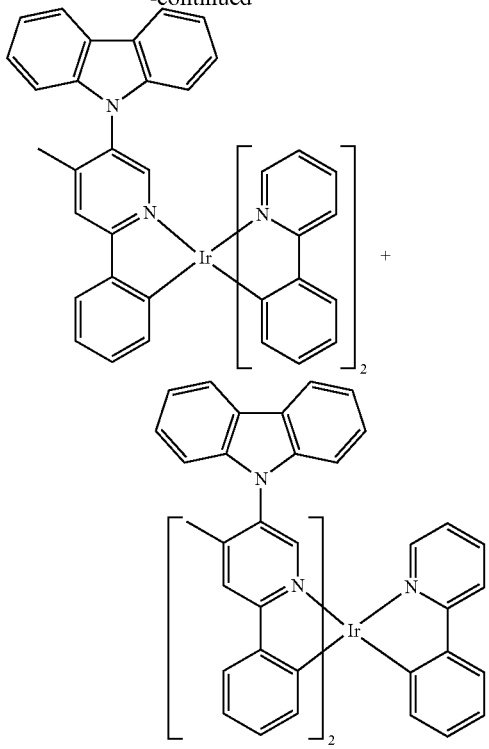

9-(4-Methyl-6-phenylpyridin-3-yl)-9H-carbazole (1.8 g, 5.38 mmol) and phenylpyridine iridium triflate intermediate (1.281 g, 1.794 mmol) were added to 50 mL ethanol and degassed by bubbling nitrogen gas for 30 minutes. Reaction mixture was heated to reflux for 48 h before being cooled to room temperature. Crude reaction mixture was filtered through a Celite pad. Precipitates were washed with ethanol followed by hexanes and finally redissolved in DCM. Organic solvents were removed under reduced pressure. Dark yellow color crude was purified by column chromatography over silica gel using 20-50% DCM/hexanes as eluent. Isolated material was repurified by reversed phase column chromatography over C18 phase using 90-95% acetonitrile/water. After sublimation Compound 4 (0.124 g) and Compound 5 (0.19 g) were isolated.

Device Examples

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound B as the hole injection layer (HIL), 300 Å of 4,4'-bis[N-(1-naphthyl)-N-phenylamino]biphenyl (alpha-NPD) as the hole transporting layer (HTL), 300 Å of heteroleptic complex of Formula (I) doped in Compound C as host with 10-15 weight percent of the iridium phosphorescent compound as the emissive layer (EML), 50 Å of Compound C as a blocking layer (BL), 400 or 450 Å of Alq (tris-8-hydroxyquinoline aluminum) as the ETL. The Comparative Example was fabricated in the same way, except that Compound A was used as the emitter in the EML instead of a heteroleptic complex of Formula (I).

Device testing results are summarized in TABLES 2 and 3. As used herein, NPD, Alq, Compound B, and Compound C have the following structures:

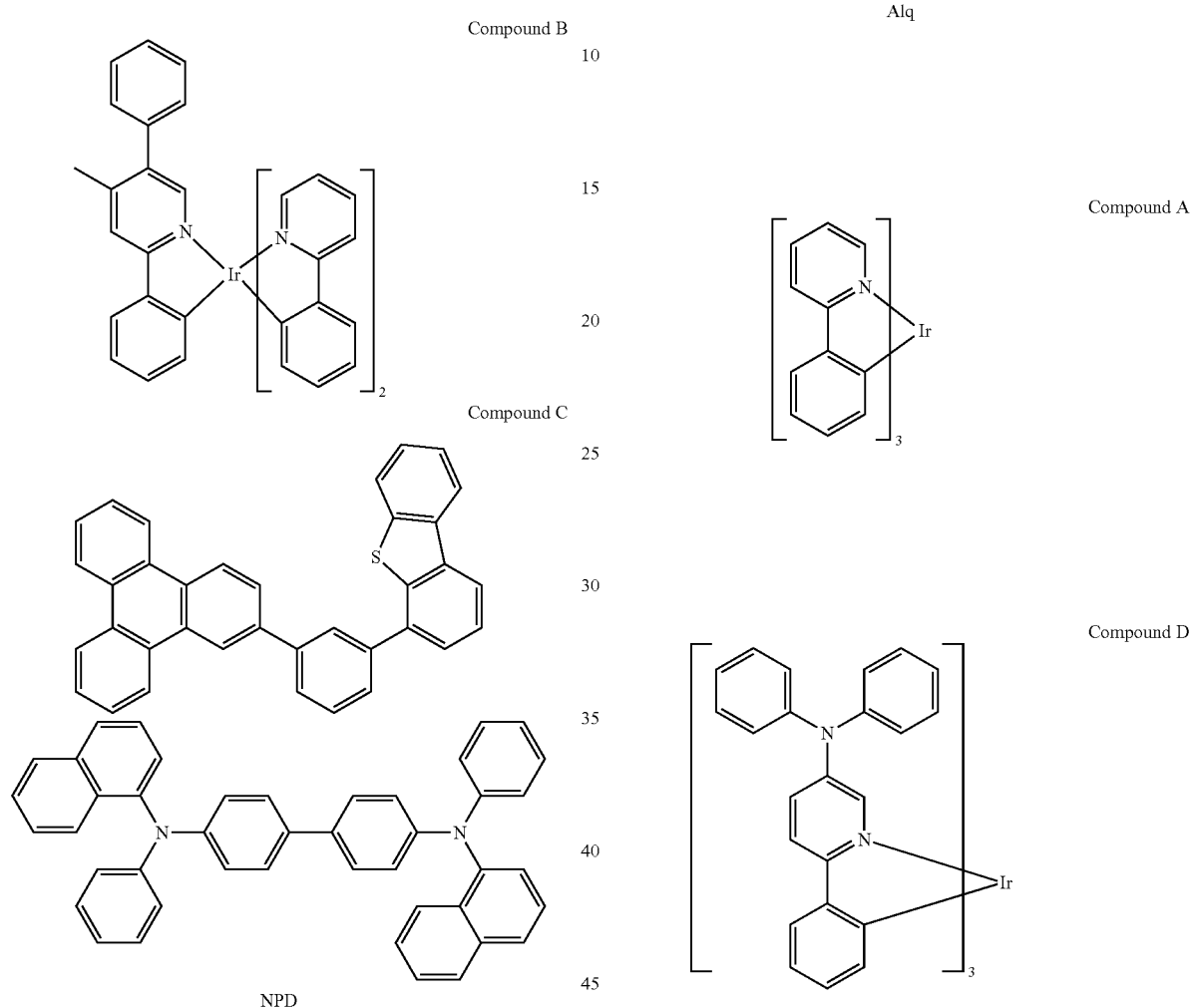
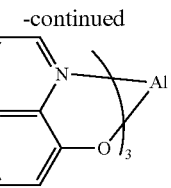

TABLE 2

Device Structures of Inventive Compounds and Comparative Compounds

| Example | HIL | HTL | EML (300 Å, doping %) | | BL | ETL |
|---|---|---|---|---|---|---|
| Example 1 | Compound B 100 Å | NPD 300 Å | Compound C | Compound 1 15% | Compound C 50 Å | Alq 450 Å |
| Example 2 | Compound B 100 Å | NPD 300 Å | Compound C | Compound 2 10% | Compound C 50 Å | Alq 400 Å |
| Example 3 | Compound B 100 Å | NPD 300 Å | Compound C | Compound 3 10% | Compound C 50 Å | Alq 400 Å |
| Example 4 | Compound B 100 Å | NPD 300 Å | Compound C | Compound 4 10% | Compound C 50 Å | Alq 400 Å |
| Example 5 | Compound B 100 Å | NPD 300 Å | Compound C | Compound 5 15% | Compound C 50 Å | Alq 400 Å |
| Comparative Example 1 | Compound B 100 Å | NPD 300 Å | Compound C | Compound A 15% | Compound C 50 Å | Alq 400 Å |

TABLE 3

| | Example 1 | Example 2 | Example 3 | Example 4 | Example 5 | Comparative Example 1 |
|---|---|---|---|---|---|---|
| CIE x | 0.412 | 0.359 | 0.394 | 0.355 | 0.349 | 0.327 |
| CIE y | 0.573 | 0.605 | 0.584 | 0.607 | 0.612 | 0.618 |
| $\lambda_{max}$ (nm) | 536 | 522 | 538 | 530 | 528 | 522 |
| FWHM (nm) | 66 | 70 | 76 | 74 | 72 | 72 |
| Voltage (V) | 5.2 | 5.7 | 6.0 | 6.1 | 5.6 | 6.2 |
| LE (Cd/A) | 67.3 | 58.6 | 59.6 | 52.3 | 47.4 | 36.1 |
| EQE (%) | 18.9 | 16.6 | 16.5 | 14.4 | 13.0 | 10.1 |
| PE (lm/W) | 40.5 | 32.2 | 31.0 | 26.9 | 26.5 | 18.4 |
| $L_0$ (nits) | 18,786 | 16,462 | 18,225 | 16,272 | 16,292 | 11,575 |
| LT80% (h) | 273 | 148 | 210 | 265 | 169 | 235 |

TABLE 3 summarizes the performance of the devices. The driving voltage (V), luminous efficiency (LE), external quantum efficiency (EQE) and power efficiency (PE) were measured at 1000 nits, while the lifetime ($LT_{80\%}$) was defined as the time required for the device to decay to 80% of its initial luminance ($L_0$) under a constant current density of 40 mA/cm$^2$.

The advantages of the inventive examples over the comparative example are both numerous and quite obvious. The inventive examples offer a wide range of green starting with inventive example 2 which displays the same $\lambda$max (522 nm) as the comparative example and approaching yellow with $\lambda$max of 538 nm (inventive example 3). Compound D decomposed upon attempted sublimation rendering it useless for the formation of VTE devices. Every one of the inventive examples 1-5 requires less voltage, i.e., 5.2, 5.7, 6, 6.1 and 5.6 V, respectively, than the comparative example (6.2 V). In every category of efficiency the inventive examples, without exception, demonstrate significantly higher device efficiencies relative to the comparative example. Looking at the luminescent efficiency for inventive examples 1-5 the values are 67.3, 58.6, 59.6, 52.3 and 47.4 (Cd/A), respectively, as compared to 36.1 Cd/A for the comparative example. The external quantum efficiency values for inventive examples 1-5 are 18.9, 16.6, 16.5, 14.4 and 13% respectively while that for the comparative example is only 10.1%. The values for power efficiency (PE) for the inventive examples 1-5 are 40.5, 32.2, 31, 26.9 and 26.5 lm/W, respectively, while that of the comparative example is only 18.4 lm/W. Inventive examples 1-5 gave initial luminance values of 18,786, 16,462, 18,225, 16,272 and 16,292 nits respectively while the comparative example gave a value of 11,575 nits. Finally all of the compounds demonstrated good stability in devices. Inventive examples 1 (273 h) and 4 (265 h) were superior to that of the comparative example (235 h).

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:

1. A first device comprising a first organic light emitting device, the first organic light emitting device further comprising:
    an anode;
    a cathode; and
    an organic layer, disposed between the anode and the cathode, comprising a heteroleptic metal complex of Formula (V):

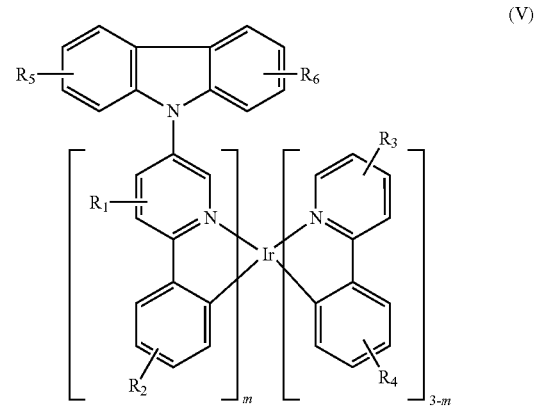

(V)

wherein $R_1$, $R_2$, $R_3$, and $R_4$ each represent mono, di, tri, tetra, or penta substitutions or no substitution;

wherein $R_5$ and $R_6$ represent no substitutions;

wherein any two adjacent substituents are optionally joined together to form a ring, which may be further substituted;

wherein each of $R_1$, $R_2$, $R_3$, and $R_4$ is independently selected from the group consisting of hydrogen, deuterium, alkyl, cycloalkyl, and combinations thereof; and wherein m is 1 or 2.

2. The first device of claim 1, wherein the heteroleptic metal complex is a compound of Formula (VI):

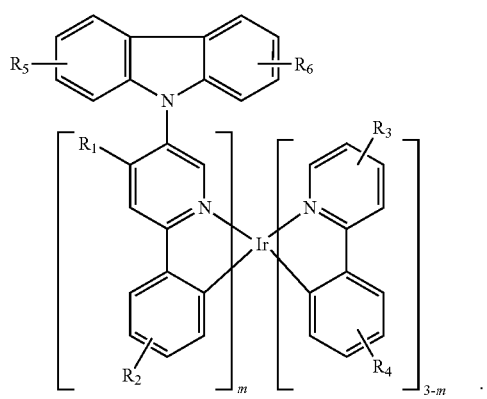
(VI)
3. The first device of claim 1, wherein m is 1.
4. The first device of claim 1, wherein m is 2.
5. The first device of claim 1, wherein the heteroleptic metal complex is selected from the group consisting of:
Compound 4
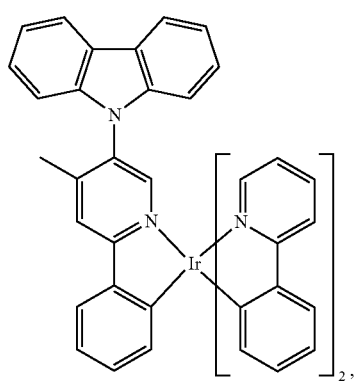
Compound 3
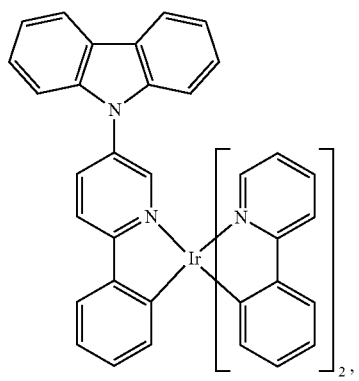
-continued
Compound 10
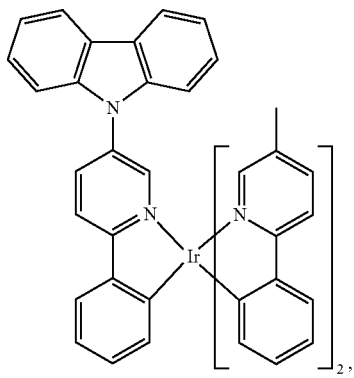
Compound 11
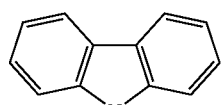
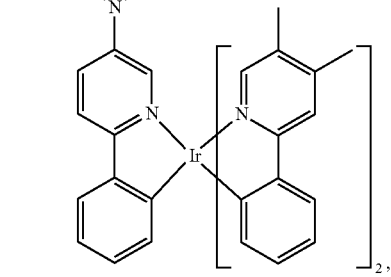
Compound 12
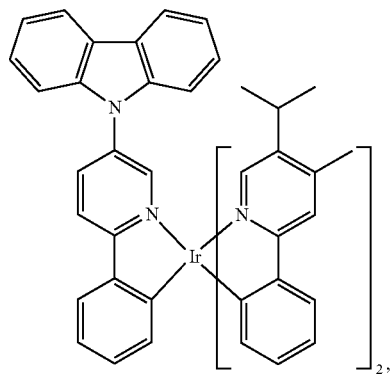
Compound 13
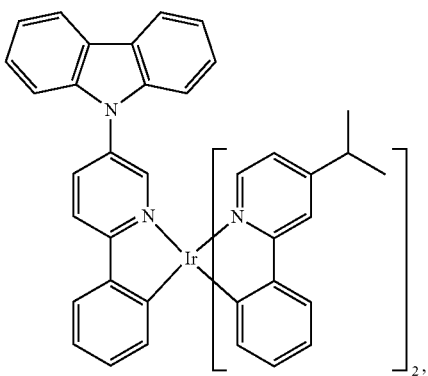

Compound 14
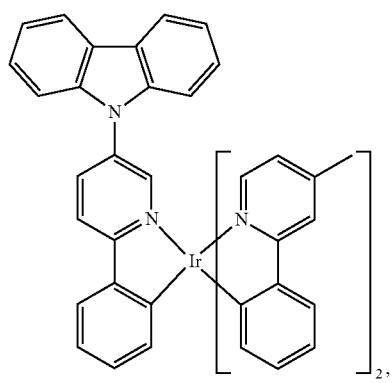
Compound 15
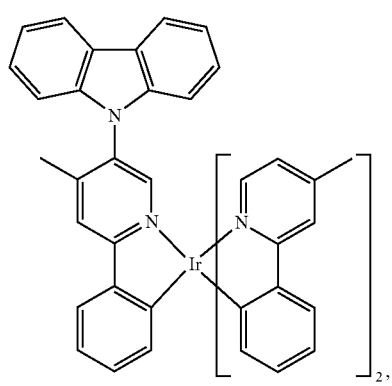
Compound 16
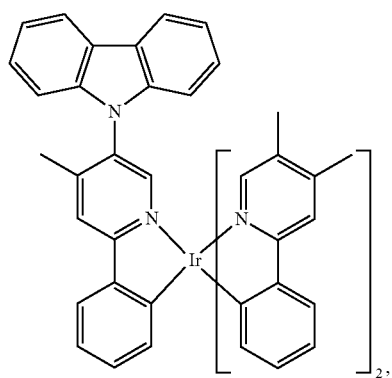
Compound 17
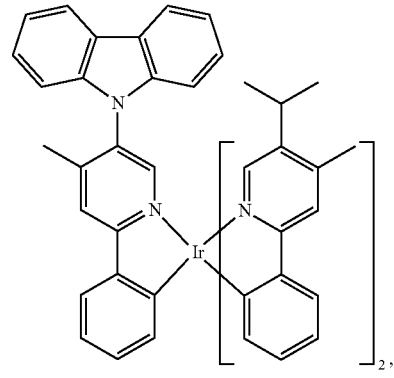
Compound 18
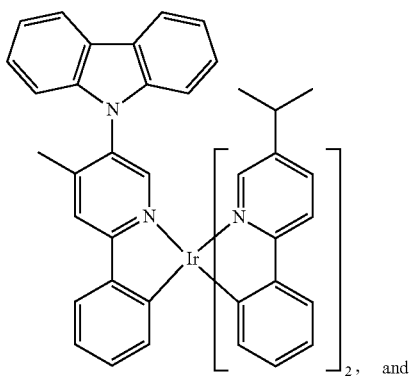
, and
Compound 19
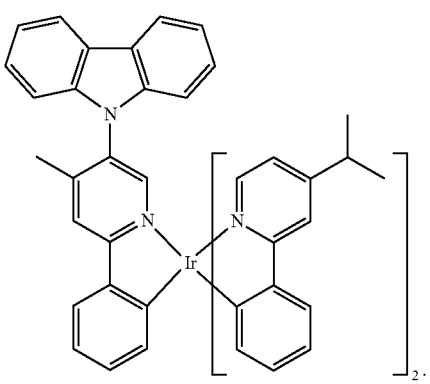
.
6. The first device of claim 1, wherein the heteroleptic metal complex is selected from the group consisting of:

Compound 5

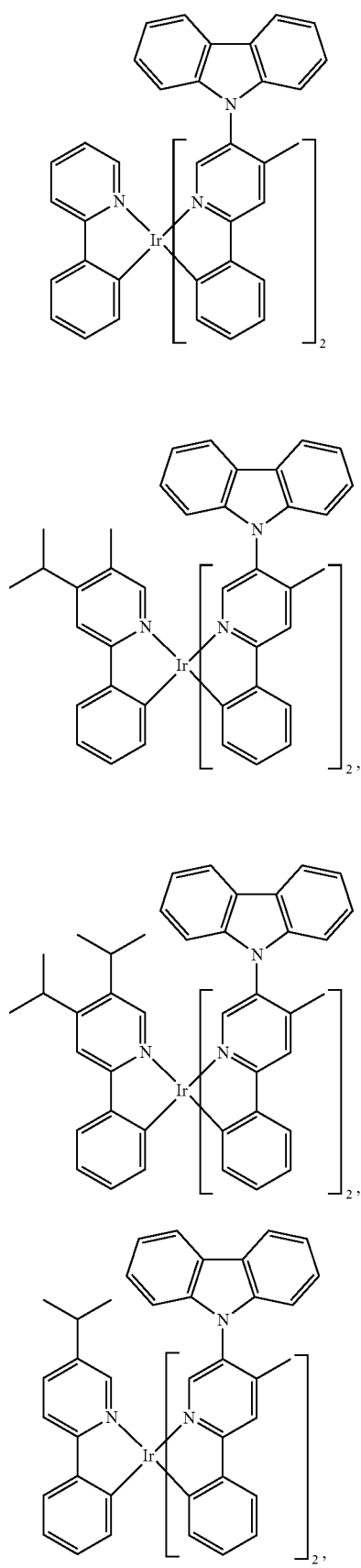

Compound 21

Compound 22

Compound 23

Compound 24

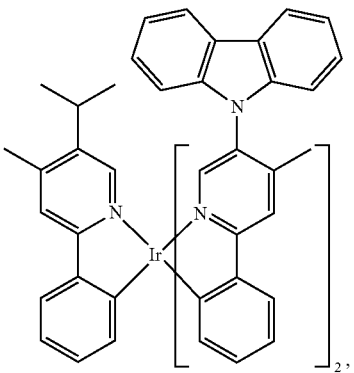

Compound 25

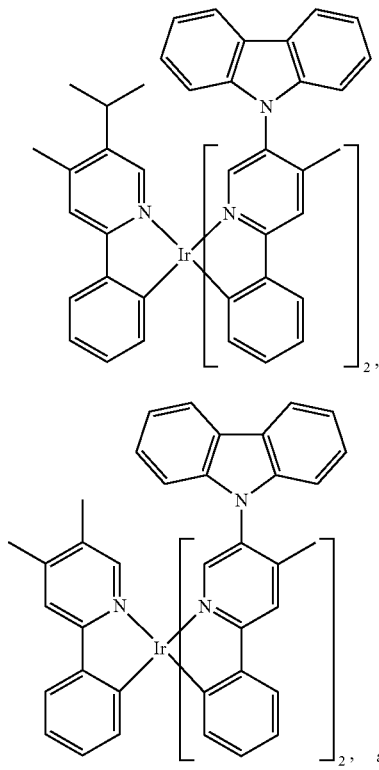

and

Compound 26

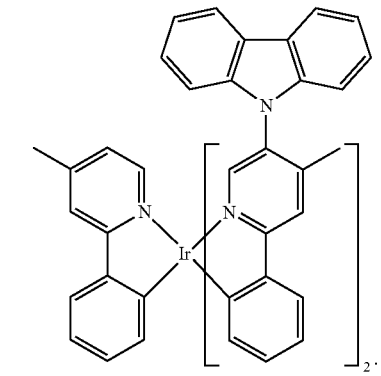

7. The first device of claim 1, wherein each of $R_1$, $R_2$, $R_3$, and $R_4$ is selected from the group consisting of: hydrogen, deuterium, methyl, ethyl, propyl, 1-methylethyl, butyl, 1-methylpropyl, 2-methylpropyl, and partially or fully deuterated variations thereof.

8. The first device of claim 1, wherein each of $R_1$, $R_2$, $R_3$, and $R_4$ is selected from the group consisting of: hydrogen, deuterium, alkyl, and combinations thereof.

9. The first device of claim 1, wherein each of $R_1$, $R_2$, $R_3$, and $R_4$ is selected from the group consisting of: hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, and combinations thereof.

10. The first device of claim 1, wherein the first device is a consumer product.

11. The first device of claim 1, wherein the first device is an organic light-emitting device.

12. The first device of claim 1, wherein the first device comprises a lighting panel.

13. The first device of claim 1, wherein the organic layer is an emissive layer and the complex is an emissive dopant.

14. The first device of claim 1, wherein the organic layer is an emissive layer and the complex is a non-emissive dopant.

15. The first device of claim 1, wherein the organic layer further comprises a host.

16. The first device of claim 15, wherein the host comprises a triphenylene containing benzo-fused thiophene or benzo-fused furan;

wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1$-$Ar_2$, and $C_nH_{2n}$—$Ar_1$;

wherein n is from 1 to 10; and wherein $Ar_1$ and $Ar_2$ are independently selected from the group consisting of benzene, biphenyl, naphthalene, triphenylene, carbazole, and heteroaromatic analogs thereof.

17. The first device of claim 15, wherein the host is selected from the group consisting of:

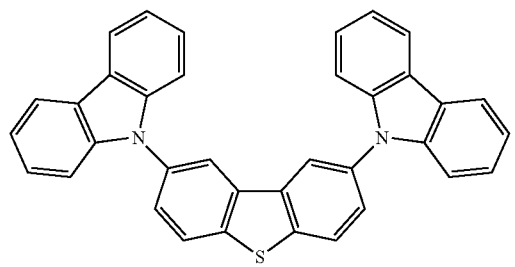

,

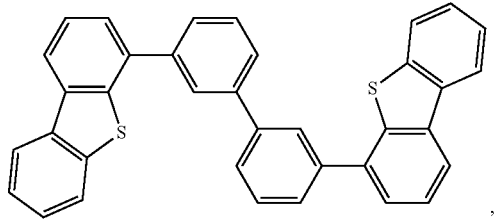

,

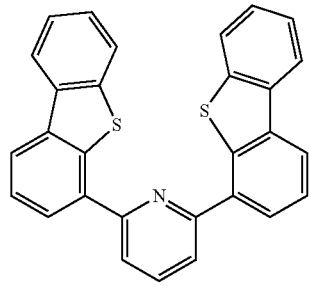

,

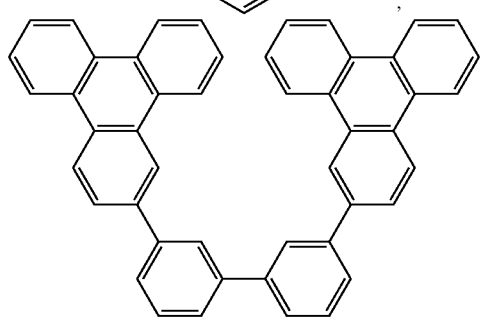

,

-continued

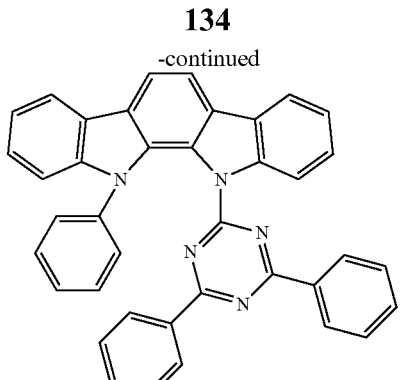

,

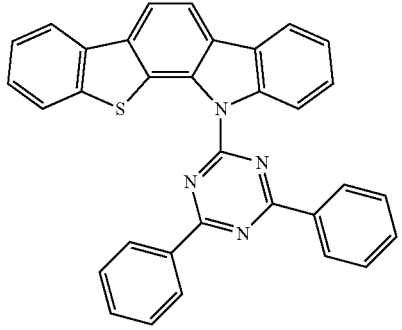

,

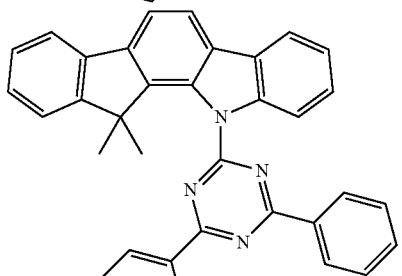

,

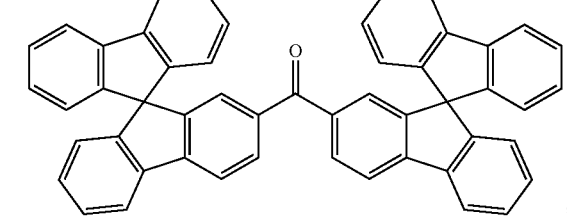

,

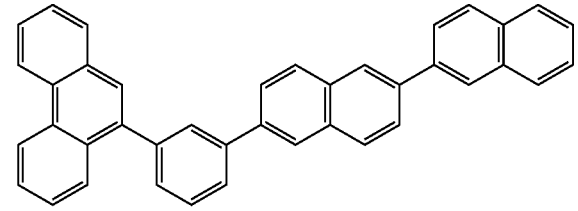

,

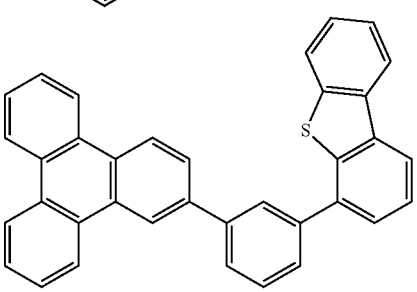

,

-continued
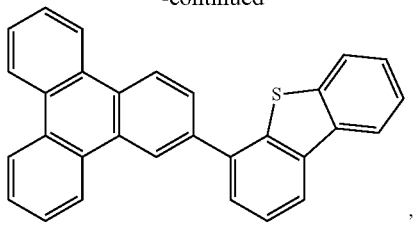
and combinations thereof.
18. The first device of claim 15, wherein the host comprises a metal complex.
* * * * *